United States Patent
Soller et al.

(10) Patent No.: US 6,663,838 B1
(45) Date of Patent: *Dec. 16, 2003

(54) HEATED VOLATILE DISPENSER

(75) Inventors: Douglas A. Soller, Racine, WI (US); Michael C. Fryan, Mount Pleasant, WI (US); Stephen B. Leonard, Caledonia, WI (US); Scott W. Demarest, Caledonia, WI (US); Steven B. Mineau, Racine, WI (US); Paul E. Furner, Caledonia, WI (US); Donald J. Shanklin, Orange, CA (US); Therese M. Nelson, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/579,409

(22) Filed: May 25, 2000

Related U.S. Application Data

(63) Continuation-in-part of application No. 09/335,370, filed on Jun. 17, 1999, now Pat. No. 6,503,459.

(51) Int. Cl.$^7$ .................................................. A62B 7/08
(52) U.S. Cl. ............................. 422/125; 422/4; 422/5; 422/120; 422/123; 422/126; 431/344
(58) Field of Search ............... 422/4, 5, 120, 422/123, 124, 125, 126

(56) References Cited

U.S. PATENT DOCUMENTS

| | | |
|---|---|---|
| 143,583 A | 10/1873 | Mayall |
| 323,548 A | 8/1885 | Valentire |
| 382,836 A | 5/1888 | Sheeley |
| 611,560 A | 9/1898 | Chambers |
| 692,075 A | 1/1902 | Searle |
| 746,942 A | 12/1903 | Feval |

(List continued on next page.)

FOREIGN PATENT DOCUMENTS

| | | |
|---|---|---|
| DE | GM 1 691 197 | 1/1955 |
| DE | 1023625 | 1/1958 |
| DE | 29720 802 U1 | 11/1997 |
| FR | 2537394 | 12/1983 |
| JP | HEISEI 5-48101 | 6/1993 |
| JP | 10-162611 | 6/1998 |
| WO | WO 92/06594 | 4/1992 |
| WO | WO 99/51912 | 10/1999 |

OTHER PUBLICATIONS 3 pages depicting the Skeeter Eater mosquito destroyer unit, undated, admitted prior art (see p. 3 of the specification).
4 pages depicitng a Japanese insect control unit, undated, admitted prior art, supplier unknown (see p. 3 of the specification).
1 page depicting another insect control unit, undated, admitted prior art, supplier unknown (see p. 3 of the specification).
1 page with photographs of another insect control unit, undated, admitted prior art, a commercial version of the product described in South African appln. 94/5537.

*Primary Examiner*—Krisanne Thornton

(57) ABSTRACT

A heated volatile dispenser and a volatile carrier for use therewith are disclosed. The volatile dispenser has a closed heating chamber having ceiling and exit vents. A fuel burner is contained within the heating chamber, and a carrier holder is positioned over the fuel burner. The carrier holder holds a volatile carrier in a location above the fuel burner such that hot gases from the fuel burner pass the carrier holder and directly heat a volatile carrier held thereby. The volatile carrier may be held in an edge-on orientation with respect to the flow of hot gases, or transversely with respect to them. The volatile carrier has an inward end that has a cross-sectional profile made to be complementary to that of an insert slot through which the volatile carrier must be inserted for use. An alternative embodiment is shown that uses a candle as a fuel burner. A kit is shown that includes a candle and a volatile carrier that are designed to be exhausted at the same time so that the candle's consumption serves as a use-cue for the volatile carrier. Methods of dispensing volatiles are disclosed.

52 Claims, 15 Drawing Sheets

U.S. PATENT DOCUMENTS

| | | |
|---|---|---|
| 1,230,342 A | 6/1917 | Thornberg |
| 1,243,439 A | 10/1917 | Myers |
| 1,547,160 A | 7/1925 | Bailey |
| 1,732,707 A | 10/1929 | Winsboro |
| 1,803,334 A | 5/1931 | Lehmann |
| 1,817,057 A | 8/1931 | Berry |
| 1,920,599 A | 8/1933 | Schuh |
| 2,293,235 A | 8/1942 | Zahner |
| 2,451,238 A | 10/1948 | Pritchard |
| 2,513,919 A | 7/1950 | Costello |
| 2,519,544 A | 8/1950 | Churchill |
| 2,611,068 A | 9/1952 | Wellens |
| 2,714,649 A | 8/1955 | Critzer |
| 2,733,333 A | 1/1956 | Peters |
| 2,742,342 A | 4/1956 | Dew et al. |
| 2,757,278 A | 7/1956 | Cloud |
| 2,813,187 A | 11/1957 | Rovira |
| 2,931,880 A | 4/1960 | Yaffe |
| 2,942,090 A | 6/1960 | Diehl |
| 3,248,530 A | 4/1966 | Titmas |
| 3,279,118 A | 10/1966 | Allen |
| 3,778,924 A | 12/1973 | Okui |
| 3,780,260 A | 12/1973 | Eisner |
| 3,948,445 A | 4/1976 | Andeweg |
| 4,251,714 A | 2/1981 | Zobele |
| 4,321,656 A | 3/1982 | Gruver, Jr. |
| 4,627,963 A | 12/1986 | Olson |
| 4,745,705 A | 5/1988 | Yamamoto et al. |
| 4,750,471 A | 6/1988 | Hautmann et al. |
| 4,781,895 A | 11/1988 | Spector |
| 4,839,144 A | 6/1989 | Martin |
| 4,849,181 A | 7/1989 | Kelley et al. |
| 5,095,647 A | 3/1992 | Zobele et al. |
| 5,111,477 A | 5/1992 | Muderlak |
| 5,168,654 A | 12/1992 | Chien |
| 5,647,052 A | 7/1997 | Patel et al. |
| 5,700,430 A | 12/1997 | Bonnema et al. |
| 5,722,199 A | 3/1998 | Demarest et al. |
| 5,744,106 A | 4/1998 | Eagle |
| 5,840,246 A | 11/1998 | Hammons et al. |
| 5,891,400 A | 4/1999 | Ansari et al. |
| 5,938,430 A | 8/1999 | Majerowski |
| 6,033,212 A | 3/2000 | Bonnema et al. |
| 6,503,459 B1 * | 1/2003 | Leonard et al. ............. 422/125 |

* cited by examiner ured within the chimney at its top, and a perforated lid closes the chimney. The lamp heats the liquid fumigant, and vapor escapes through the perforations of the lid. Handling the uncontained liquid fumigant and gaining access to and refilling the cup can be inconvenient and risk spillage.

HEATED VOLATILE DISPENSER

CROSS-REFERENCE TO RELATED APPLICATIONS

This is a continuation-in-part of U.S. patent application Ser. No. 09/335,370, filed Jun. 17, 1999, now U.S. Pat. No. 6,503,459.

STATEMENT REGARDING FEDERALLY SPONSORED RESEARCH/DEVELOPMENT

Not Applicable

BACKGROUND OF THE INVENTION

The present invention relates to dispensers for volatiles such as scents, insect control active ingredients, and the like. In particular, it relates to such dispensers that use a fuel burner.

There are a variety of known dispensers for volatiles that employ heat from a flame or from catalyzed combustion to dispense volatiles from volatile-impregnated substrates. Citronella candles mix the volatile into the fuel itself. However, this leaves the candle flame exposed.

U.S. Pat. No. 692,075 shows the use of heat from the flame of a conventional oil lamp to dispense volatile ingredients held exposed to the ambient air on a mesh mounted on a lamp chimney, above the lamp's flame. The disclosure of this patent and of all other publications referred to herein are incorporated by reference as if fully set forth herein. The volatile material being heated by this device is positioned above the lamp chimney and thus is directly exposed to ambient air currents, which can cause uneven heating and cooling of the volatile material. The exposed location of the material being heated also allows it to be touched or disturbed by a passing child or animal. Furthermore, it is immediately visible to a user so that charred material can present an unsavory sight.

U.S. Pat. No. 143,583 discloses a fumigator in which an alcohol lamp is placed at the bottom of a metal chimney. A cup to hold an otherwise uncontained liquid fumigant is suspended within the chimney at its top, and a perforated lid closes the chimney. The lamp heats the liquid fumigant, and vapor escapes through the perforations of the lid. Handling the uncontained liquid fumigant and gaining access to and refilling the cup can be inconvenient and risk spillage.

Petzwinkler, South African patent abstract 94/5537, discloses an oil lamp equipped with a metal mosquito mat holder that is positioned beside, as opposed to over, the lamp's flame. Heat radiating from the flame heats a metal holder from that side of the holder which is presented toward the flame. A conventional mosquito mat is then held vertically on the opposite side of the holder, away from the flame. By this means, the mat is shielded from direct exposure to the flame or its gases, albeit it is heated to drive off the volatiles contained in the mat.

The Petzwinkler dispenser provides a visible flame. However, this dispenser has a mosquito mat holder that holds a mat beside the flame, in open view of a user, detracting from the pleasing visual effect of the flame itself. Also, one must remove the dispenser's chimney to gain access to a spent mat to replace it.

U.S. Pat. Nos. 5,700,430 and 3,778,924 each employ butane as a fuel for a flame or a catalytic burner, using a replaceable fuel tank. In U.S. Pat. No. 5,700,430 mosquito mat is laid on top of a metal plate. Heat is conducted from the location of a flame to the metal plate by means of intervening, heat-conductive parts. In a subsequent version of the device that otherwise closely corresponded to the embodiment shown, a butane flame was enclosed within a metal, rectangular, open-ended box. The box was heated by the flame, and the flame's gases exited an open end of the box to be vented from the device. A mosquito mat was positioned on top of the box to receive heat conducted through the metal box from the flame. The butane flame, heat-conductive parts, and mosquito mat were all held within a protective heat box.

U.S. Pat. No. 5,700,430 thus relies on indirect heating. The volatiles from the hottest places on the mat are released fastest. Consequently, the mat's volatiles are discharged unevenly, with the possibility that volatiles at locations remote from the hottest places may never be discharged before the mat's overall release rate becomes so low as to require replacement of the mat.

In U.S. Pat. No. 3,778,924 a mosquito mat is held exposed to the ambient air on a metal sole plate over a catalytic burner fueled by butane drawn from a replaceable, pressurized tank. However, the mat is not enclosed in a heating chamber.

Other patents disclose assemblies that rely on an electrical heater (as distinguished from a fuel burning heater) to heat the volatile carrier. See e.g. U.S. Pat. Nos. 2,513,919, 2,942,090, 4,849,181 and 5,111,477. This restricts the portability of the device (it cannot easily be used at camping or picnic sites which do not have electrical power).

U.S. Pat. No. 5,722,199 discloses a flea trap (without a volatile heater) having a removable tray that slides into a slot in the flea trap. The slot has keying structures that restrict access into the slot. To enter, a tray must present a complementary cross-sectional profile to the slot.

There are also a number of other known insect repellent/killing devices which provide a heat source under a platform designed to support a pad that has been impregnated with the insect control active ingredient. Some use a liquid fuel such as alcohol that is burned in an open flame, or directed to a catalyst mesh where it combusts.

In some cases the platform is an open grid. In others it is a flat metal plate heated from beneath. Some of these systems also provide a separate grid structure which snaps or swings over the carrier for restricting access to the heated mat during operation. These systems typically do not provide a light source through transparent sides of a heating chamber (e.g. they are designed purely for insect control).

It can therefore be seen that there is a need for an improved heated volatile dispenser.

BRIEF SUMMARY OF THE INVENTION

The invention provides a heated volatile dispenser for dispensing volatile ingredients from a volatile carrier. "Volatile ingredients" include (without limitation) perfumes and other air quality modifying materials, as well as insect control ingredients. "Insect" includes arachnids and other similar, small animals commonly controlled in conjunction with insects. "Insect control ingredients" are defined as including (without limitation) insecticides, repellents, and other development or behavior modifying materials. One highly preferred insect control agent is d-cis/trans allethrin.

A "volatile carrier" is a material or structure for holding a volatile ingredient for dispensing. "Mats" are one common type of volatile carrier often used with insect control ingredients and are defined as including (without limitation) woven, felted, or otherwise formed fibrous or cellulose materials; as well as molded, extruded, cast, or otherwise formed polymeric, ceramic, and clay materials, together with other convenient materials loaded with volatile ingredients, whether by impregnation, printing, or otherwise. Volatile carriers can also be metal or plastic cups holding a volatilizable gel; cups holding a gel, powder, or liquid retained in the cup by a volatile-permeable membrane; or any other convenient means for holding a material to be volatilized by the application of heat. However, uncontained liquids or powders, together with liquids or powders held in open cups or similar containers, are excluded from the term "volatile carrier," as used herein.

In one form, the heated volatile dispenser of the invention has an enclosed heating chamber having chamber walls. The heating chamber preferably also has a ceiling, although a heating chamber will be understood as being "enclosed" if it has walls, either an open top or a ceiling, and either a closed or an open bottom. If the heating chamber has a ceiling, the heating chamber also has exit vents in the ceiling or chamber walls or both that communicate between the interior of the heating chamber and the outside air. The exit vents are holes, slots, or other openings that function as vents. Particularly preferred are permanently enclosed structures with ceilings.

The dispenser also has a heat source that preferably is a fuel burner. The fuel burner can be a candle, a burner using a solidified combustible liquid such as conventional gelled alcohol, a burnable solid, a pressurized gas burner, a wick that is fueled with a combustible liquid, a catalytic heater burning a gas or liquid fuel, or any other convenient means for combusting a fuel.

The heated volatile dispenser is equipped to hold a volatile carrier contained within the heating chamber. It is possible to design a volatile carrier that requires no separate, specific structure in the dispenser to hold it within the heating chamber—for example, a volatile carrier equipped with side hooks or arms that hook over the tops of the heating chamber walls, allowing the rest of the volatile carrier to hang downwardly within the heating chamber. Such side hooks, together with the surface that supports them, would constitute a carrier holder. However, it is preferred that the heated volatile dispenser include an additional structure that serves as a carrier holder that is positioned to receive and hold a volatile carrier at a location above the fuel burner and contained within the heating chamber. An air-flow path is provided to guide hot gases, rising from the fuel burner by convection, past the location where a volatile carrier can be held, whether or not in a separate carrier holder, to heat the volatile carrier. The air-flow path is preferably defined, at least in part, by internal surfaces of the heating chamber walls. Heating is accomplished by the direct exposure of the volatile carrier to gases heated by the fuel burner. Preferably, the hot gases include combustion products from the fuel burner. The air-flow path then directs the hot gases through the open top of an open-topped heating chamber or through the exit vents, if a ceiling is present, to escape from the dispenser. As the volatile carrier is heated by the gases, volatile material is released and is carried out of the dispenser with the escaping hot gases.

As indicated above, the term "carrier holder" should be understood very broadly as including any structure that provides for positioning a volatile carrier within the air-flow path, within the heating chamber. In some embodiments, very little separate structure is actually required. For example, in one form, the carrier holder can be a slot in the heating chamber wall through which a volatile carrier is inserted, with the slot being a sufficiently snug fit for the volatile carrier that the parts of the volatile carrier projecting within the heating chamber are held in position by the snug contact between the slot and the volatile carrier. Also, a possible carrier holder can be a slot in the heating chamber ceiling, for use with a volatile carrier that is designed to be inserted downwardly through the slot and to hang from the edges of the slot from side tabs, a handle, or other parts of the volatile carrier that, because of their size or geometry, remain outside of the heating chamber, resting on outer surfaces of the ceiling.

Alternatively, the carrier holder may be an essentially open, either vertically or horizontally disposed rack that leaves a mat or other volatile carrier held in the carrier holder directly exposed to hot gases rising in a convective flow from beneath. Alternatively, the carrier holder can be a generally horizontal heat-conductive sole plate that supports the volatile carrier. While the upper surface of the volatile carrier remains directly exposed to the hot gases from the fuel burner, the under surface of the volatile carrier is in contact with and heated by the sole plate, with the under side of the sole plate being exposed to the flow of hot gases from the fuel burner or to heat otherwise received from the fuel burner.

Depending on the materials chosen and the volatile carrier temperatures desired, it is also possible to include a baffle spaced from and preferably located beneath the carrier holder and interposed between the fuel burner and a volatile carrier being held in the carrier holder. The baffle functions in part to mix hot gases from the fuel burner with air in the heating chamber prior to their reaching the volatile carrier. The result is believed to be a reduction of the tendency for a hot spot to form at a point on the volatile carrier directly above the fuel burner. Instead, the baffle causes a more even heating of the volatile carrier, whether the volatile carrier is heated solely by direct exposure to the hot gases or by a combination of direct exposure to hot gases and heat conducted through a sole plate.

The baffle can also function to more evenly distribute heat in another way. If the baffle is so located as to be heated by hot gases contacting the baffle from below, and if the carrier holder is spaced above the baffle, then the hot baffle serves as a radiant heater, supplementing heat delivered by a volatile carrier's direct contact with the hot gas flow by providing broadly distributed radiant heat to the volatile carrier.

Alternatively, the carrier holder can be in the form of an oven located within the heating chamber. "Oven" shall mean any substantially enclosed sub-chamber located within the heating chamber walls and made, preferably, of a heat-conductive material. The oven has oven walls and is positioned within the air-flow path. By this arrangement, the oven is heated by hot gases rising from the fuel burner. The oven holds a volatile carrier within the oven to receive heat radiating inwardly from the oven walls, an arrangement that provides for a more even heating of the volatile carrier. The oven preferably has openings sufficient to admit hot gases rising from the fuel burner so that they may directly contact the volatile carrier, and in any event has vents to allow volatile materials released from the volatile carrier to escape from the oven.

Although the fuel burner can be located beneath a heating chamber that has an open bottom, preferably the fuel burner is contained within the heating chamber itself. This arrangement contributes to the control and isolation of the convective flow of hot gases rising from the fuel burner and can also provide containment and protection for a burning flame. Thus, the walls of the heating chamber above the fuel burner can define the air flow path and limit the effects of breezes and other air movement external to the volatile dispenser.

It is sometimes desirable to reduce the temperature of the hot gases prior to their acting to heat the volatile carrier. To help achieve this, the heating chamber walls can be equipped with cooling vents communicating with the air outside of the heating chamber to cause unheated air to be drawn into the heating chamber by the passing flow of heated gases, to mix with and partially cool the hot gases from the fuel burner prior to their reaching the carrier holder. The cooling vents can be provided at any point in the air flow path, but preferably they are located at a point in the chamber walls at or above the level of the fuel burner but beneath the level at which a volatile carrier is held.

Although the fuel burner may burn fuel catalytically or otherwise without a flame and still fall within the breadth and scope of the invention, it is highly preferred that the fuel burner support a luminous flame positioned within the heating chamber and that the heating chamber walls include a light-transmitting portion, whether clear or translucent, that allows light from the flame to be visible to a user of the dispenser. This provides a ready means for a user to confirm that the fuel burner has been lit and continues to burn, and it also provides a use-up cue for the fuel. But the flame also provides light and aesthetic appeal, in much the same way that a citronella candle is valued in great part for its light. However, it is preferred that the carrier holder be positioned within a portion of the heating chamber whose walls are opaque or translucent so that the holder is at least not clearly visible through the chamber side walls. Walls will be deemed "visually obstructed" if they are opaque, translucent, or otherwise prevent the observation of distinct outlines of objects viewed therethrough.

The mats or other volatile carriers become exhausted and are designed to be replaced. To achieve this, preferably an insert slot communicates between the interior of the heating chamber and the exterior of the heated volatile dispenser, so that a fresh volatile carrier can be inserted through the insert slot to be held by the carrier holder. The insert slot can be in either the chamber walls or the ceiling of the heating chamber.

It can be important to prevent the use of a volatile carrier not intended for use with a particular volatile dispenser, to not mistakenly use, for example, a volatile carrier loaded with insecticide in a dispenser intended to supply perfume for indoor use. Therefore, it is preferred that the insert slot include keying structures that impart a cross-sectional profile to the insert slot that so restricts access thereto as to prevent the insertion of any volatile carrier not capable of presenting a non-interfering cross-sectional profile to the cross-sectional profile of the insert slot. This makes it easier to ensure that the only volatile carriers that will fit a given dispenser are those that are appropriate to a particular purpose or that are designed for use with the specific temperatures generated by the volatile dispenser. Also, the keying structures can be used to require that the volatile carrier be insertable only with a pre-determined side up or down. This can be important if the volatile carrier is, by way of example only, a gel cup that must be inserted so as to open upwardly. As examples, the keying structures can define a cross-sectional profile that includes either or both of angularly intersecting and curved sections.

Volatile carriers have a section treated or loaded (e.g. paper impregnated with insecticide) with the volatile material to be dispensed, and this section may itself be formed with a functionally required cross-sectional profile such as those just described. Alternatively, the volatile carrier can include a handle in addition to a volatile-treated section, and the keying structures of the insert slot can be formed to present a non-interfering cross-sectional profile with respect to at least a portion of the volatile carrier and an interfering cross-sectional profile with respect to the handle for the volatile carrier.

In one embodiment, the heated volatile dispenser includes a fuel tank, containing fuel under pressure, and a fuel transfer route by which fuel can be transferred to the fuel burner in controlled amounts. Valves, constricted flow paths, wicks, pressure step-down controllers, or any other means may be used to control the delivery of pressurized fuel to the fuel burner in an amount sufficient to maintain combustion at a convenient level, and a variable valve may be used to allow a user to adjust the amount of fuel being burned. Preferably the fuel tank is replaceably removable. Ideally, the fuel tank contains fuel that burns as a pressurized gas, even though it may be a liquid at the tank pressures selected. Preferred gases include a gas selected from the group consisting of butane, isobutane, propane, compressed natural gas, and mixtures thereof.

An alternative and presently most preferred embodiment of the heated volatile dispenser of the invention is designed for use with a volatile carrier having a volatile-loaded section having a linearly extended volatile-releasing surface. The heated volatile dispenser includes a heat source that preferably is a fuel burner, the heat source generating a convective flow of hot gases. The heated volatile dispenser can be used with a volatile carrier designed to hang or otherwise be positioned within the flow of hot gases in an orientation such that hot gas sweeps across the volatile-releasing surface, preferably in a generally vertical direction but, in any event, in a direction generally parallel to the direction of linear extension of the volatile-releasing surface to release volatile therefrom. Preferably, the heated volatile dispenser includes a carrier holder that holds the volatile carrier within the flow of hot gases in that orientation. The heated volatile dispenser can also have any or all of the other features disclosed, above, with respect to the other embodiments, so long as those features are not inconsistent with the orientation of the volatile carrier just described.

Preferably a volatile carrier is used that has at least two volatile-releasing surfaces. The volatile carrier is then so designed, or the carrier holder, if present, then is designed, to hold the volatile carrier in an orientation such that hot gas sweeps across at least two of the volatile-releasing surfaces at the same time. Most conveniently, the volatile carrier has front and back volatile-releasing surfaces. By way of example, only, a conventional mosquito mat has front and back surfaces, and the volatile carrier or the carrier holder can be designed such that the mat is held edge-on with respect to the flow of hot gases so that gas sweeps across both surfaces of the mat at the same time.

This arrangement has important advantages for the control of temperature across the volatile-releasing surfaces of the volatile carrier. The convective flow of hot gases above a sufficiently hot heater, and especially above a fuel burner that produces both heated air and gaseous combustion products, is fast compared to the conductive flow of heat through metal or other solid materials. Consequently, it is believed that the temperature of the hot gases does not drop much as the gases pass over the volatile-releasing surfaces. As a result, the volatile carrier is more evenly heated across its linear expanse so that volatiles are released more uniformly from the entire volatile-releasing surface. When the rate of volatile release from the volatile carrier drops sufficiently low that a fresh carrier is needed, the volatile from the exhausted carrier will have been more completely used than is the case when distinct, hotter and cooler regions are formed across the volatile-releasing surfaces.

When the heated volatile dispenser includes a carrier holder that is designed to be used with a volatile carrier having a linearly extended, volatile treated section having a leading edge to be presented toward the flow of hot gases, the carrier holder should preferably include a heat resistant edge guard that extends along the leading edge of a volatile carrier held in the carrier holder. The edge guard preferably extends the entire length of the leading edge. Alternatively, the edge guard can extend to protect only a portion of the leading edge that is exposed to the hottest area within the flow of hot gases, typically located at the center of the leading edge. An edge guard or a material will be understood to be "heat resistant" if it does not burn, char, or deform when subjected to the temperatures present at its location within a heated volatile dispenser when that dispenser is in use.

The edge guard protects the leading edge of the volatile carrier from heat directly radiating from a fuel burner and from the direct, edgeward impact of the flow of hot gases. Also, when the volatile carrier has at least two and preferably front and back volatile-releasing surfaces, the edge guard helps to split the flow of hot gases to direct the gases across the volatile-releasing surfaces. Either additionally or alternatively, a volatile carrier of the invention intended for such an edge-on orientation can be equipped with a carrier edge guard formed on or attached to the leading edge of the volatile carrier, itself. It is preferred that the edge guard, whether a part of the heated volatile dispenser or attached to the leading edge of the volatile carrier, include deflector vanes extending sidewardly with respect to the direction of linear extension of the volatile carrier's treated section to disrupt and mix the flow of hot gases before the gases contact the treated section.

In the presently most preferred embodiment of the invention, fuel burner is ventilated from beneath via a circumferentially extending open space surrounding the fuel burner, which space is vented to the ambient air. When a base is provided, located beneath the heating chamber, the base has a ventilation opening through which ambient air can pass to continue upwardly through the heating chamber. The fuel burner is so supported by the base in relation to the ventilation opening that the fuel burner is circumferentially ventilated from beneath. The preferred fuel burner in this arrangement employs a candle and preferably includes a candle cup having cup walls and a downwardly opening socket. The base then includes an attachment post to engage the socket and thus hold the candle cup. The heating chamber can include a light-transmitting chimney attached to the base.

Although the volatile dispenser of the invention (and preferably the embodiment just described) can be made with a base that can rest in a stable fashion on a flat supporting surface, it is also possible to provide for hanging the dispenser from a hook or other supporting structure. In that arrangement, the heated volatile dispenser includes a hanger by which the dispenser may be suspended from above. It is also then possible to so shape the underside of the base as to prevent the dispenser being supported in an upright orientation on a flat surface.

It is beneficial to provide for a candle that self-extinguishes, should the volatile dispenser tip over. To achieve this result, the fuel burner includes a candle contained within a candle cup, the candle cup having a floor and upright walls terminating in an open top and being made of a heat resistant material. The candle cup is fixedly positioned within the heating chamber, so that, should the volatile dispenser tip sidewardly while the candle is burning, the candle's heat contained within the candle cup will melt at least a portion of the candle's wax, allowing it to flow from the open top to starve the candle's wick of fuel, causing the candle to self-extinguish.

A method for dispensing ingredients volatilizable by application of heat includes the steps of providing a heated volatile dispenser having an enclosed heating chamber capable of holding a volatile carrier therewithin, the heating chamber having chamber walls and being vented to the outside air. The heated volatile dispenser so provided also has a fuel burner and an air-flow path to guide hot gases from the fuel burner past a volatile carrier held within the heating chamber to heat the volatile carrier by the direct exposure of the volatile carrier to the hot gases, the air-flow path then directing the hot gases to escape from the dispenser to the outside air. The method includes the further steps of positioning a volatile carrier loaded with ingredients to be volatilized in the flow of hot gases; igniting fuel at the fuel burner; and allowing the volatile carrier to be heated and the ingredients thus volatilized therefrom to be vented from the dispenser. The step of igniting the fuel can be performed at any convenient point in the method.

An alternative and preferred method of the invention is disclosed for dispensing a volatile material from a volatile carrier having a volatile-loaded section having a linearly extended, volatile-releasing surface. The method includes the steps of providing a heat source, preferably a fuel burner, generating a flow of hot gases and holding the volatile carrier within the flow of hot gases in an orientation such that hot gas sweeps across the volatile-releasing surface, preferably in a direction generally parallel to the direction of linear extension of the volatile-releasing surface. Preferably, the volatile carrier has at least two and preferably both front and back volatile-releasing surfaces, and the step of holding the volatile carrier within the hot gases includes holding the volatile carrier in an orientation such that hot gas sweeps across at least two and preferably both the front and back volatile releasing surfaces at the same time.

The invention also includes a volatile-dispensing volatile carrier suitable for use with a heated volatile dispenser having an insert slot through which the volatile carrier must be inserted for use, the insert slot having keying structures that impart a cross-sectional profile to the insert slot that departs from a straight cross-sectional profile and that so restricts access thereto as to prevent the insertion of any volatile carrier not capable of presenting a complementary cross-sectional profile. The volatile carrier of the invention includes a treated section having a cross-sectional profile complementary to that of the insert slot. The volatile carrier also can have a handle having a cross-sectional profile that prevents the handle's entrance into the insert slot. Preferably the cross-sectional profile of the treated section includes curved or angularly intersecting sections, the latter including (without limitation) slots, prongs, ribs, and the like. Combinations of curved and angularly intersecting sections may also be used. Preferably the volatile carrier is a mat.

A kit is also disclosed for use with a heated volatile dispenser that employs a fuel burner to provide hot gases to heat and release a volatile material from a volatile carrier. The kit includes at least one volatile carrier, each volatile carrier bearing a selected amount of the volatile to be dispensed, and at least one fuel source for the fuel burner. The amount of fuel in a selected number of fuel sources is selected to be exhausted at substantially the same time that a selected amount of the volatile has been exhausted from at least one of the volatile carriers of the kit, whereby the exhausting of fuel provides a use up cue indicating that the selected amount of volatile has also been exhausted. Volatile is defined as being "exhausted" if the volatile has been released to the point that additional release of volatile is reduced to an amount or rate such that the desired effect to be accomplished by the volatile release is no longer achieved. A fuel source is defined as being exhausted at "substantially the same time" as the volatile is exhausted if the fuel burner extinguishes for lack of fuel when the volatile is either exhausted or when only that amount of volatile remains that a user is willing to discard.

Preferably, the kit includes only paired single fuel sources and single volatile carriers, with the volatile of a single volatile carrier being exhausted by the hot gases generated by the use of a single fuel source. However, it is also possible to achieve the benefit of the invention by requiring that two or more fuel sources be used before the volatile of a given carrier is exhausted. The goal is to have the easily perceived consumption of fuel serve as a use-up cue for the less easily detected consumption of the volatile of a volatile carrier. Preferably, the fuel source is a candle.

Preferably, the volatile carriers of the kit have a treated section that is linearly extended and holds volatile material to be dispensed, and the amount of volatile material held by a volatile carrier is selected to be exhausted by the hot gases generated by the use of a single fuel source when the volatile carrier is so positioned that the hot gases sweep over the linearly extended section. In an even more preferred embodiment, the treated section has at least two sides and the amount of volatile material held by a volatile carrier is selected to be exhausted by the hot gases generated by the use of a single fuel source when the volatile carrier is so positioned that the hot gases sweep over the at least two sides of the linearly extended section. Ideally, the treated section has at least two sides (preferably a front and a back), and the volatile carrier has a leading edge. The amount of volatile material held by the treated section is selected to be exhausted by exposure to a flow of hot gases generated by the use of a single fuel source when the volatile carrier is so positioned that the flow of hot gases divides, with hot gases flowing to either side of the leading edge, to sweep over the sides of the treated section.

The invention also includes a method of dispensing a volatile material from a volatile carrier by use of a heated volatile dispenser of the sort that utilizes a fuel burner to generate a flow of hot gases over the volatile carrier to release volatile material therefrom. The method includes a first step of providing a fuel source for the fuel burner having an amount of fuel selected to become exhausted (causing the fuel burner to extinguish) at the same time that the volatile of the volatile carrier is substantially exhausted. The effect of this step is to cause the extinguishing of the fuel burner to provide a use-up cue for the substantial exhaustion of volatile from the volatile carrier. The second step of the method is to light the fuel burner, with the volatile carrier in place. Preferably, the heated volatile dispenser used is of the sort in which fuel burns as a flame visible to a user of the dispenser. In that event, the steps of providing the fuel source and lighting the fuel burner include providing a visually observable use-up cue for the substantial exhaustion of volatile from the volatile carrier.

Also provided is a fuel burner useable with a heated volatile dispenser that has an attachment post for holding the fuel burner. The fuel burner includes a candle held within a open-topped candle cup. The candle cup has a cup floor, cup walls, and a downwardly opening socket extending downwardly beneath the cup floor and engageable on the attachment post. At least one cup support member extends downwardly beneath the cup floor at least as far as the socket extends. The at least one cup support member is at a location sufficiently remote from the socket and cumulatively extends circumferentially sufficiently to provide a stable support such that the candle cup can sit on a flat surface without tipping. Preferably, the cup support member extends around the entire margin of the cup floor. This arrangement is generally convenient for a user, but it is also important in the manufacture of the fuel burner in that it allows the candle cup to sit in a stable fashion on a flat conveyer belt or other materials handling surface.

DETAILED DESCRIPTION OF THE INVENTION

Figure 1:
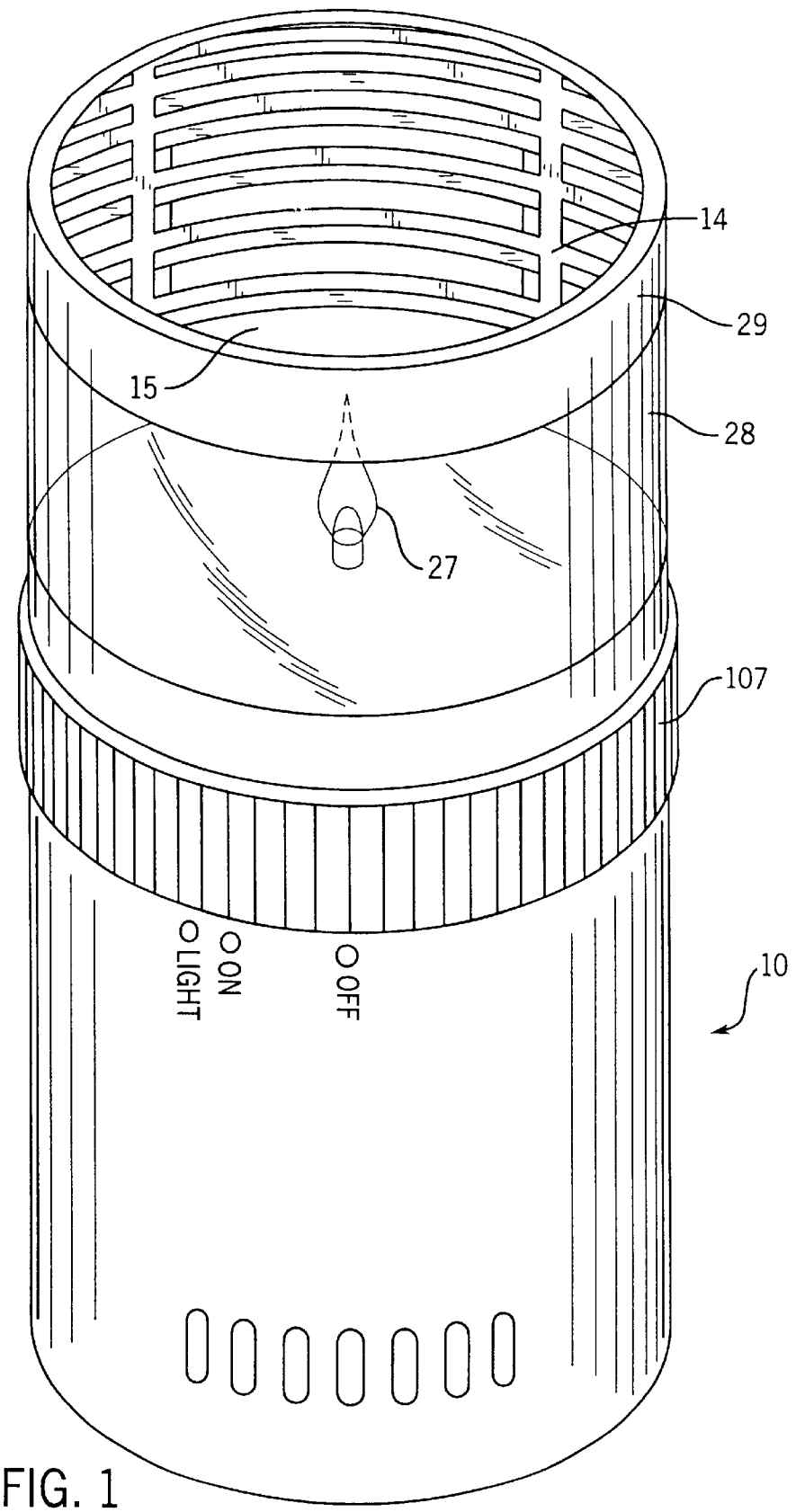
FIG. 1 is a perspective view of a heated volatile dispenser of the invention which uses a gas fuel source.
Figure 2:
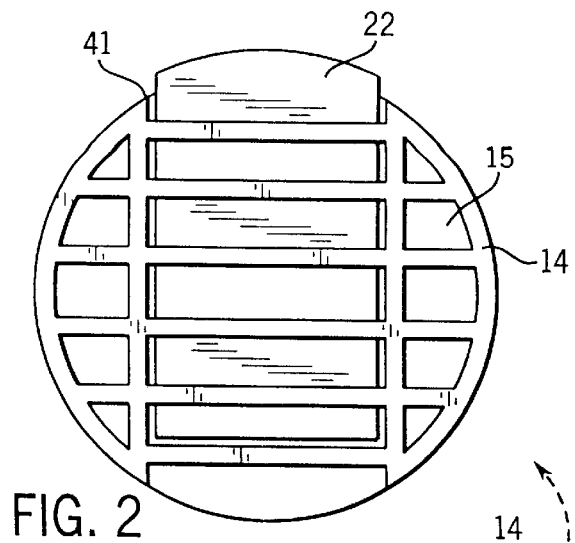
FIG. 2 is a top plan view thereof.
Figure 3:
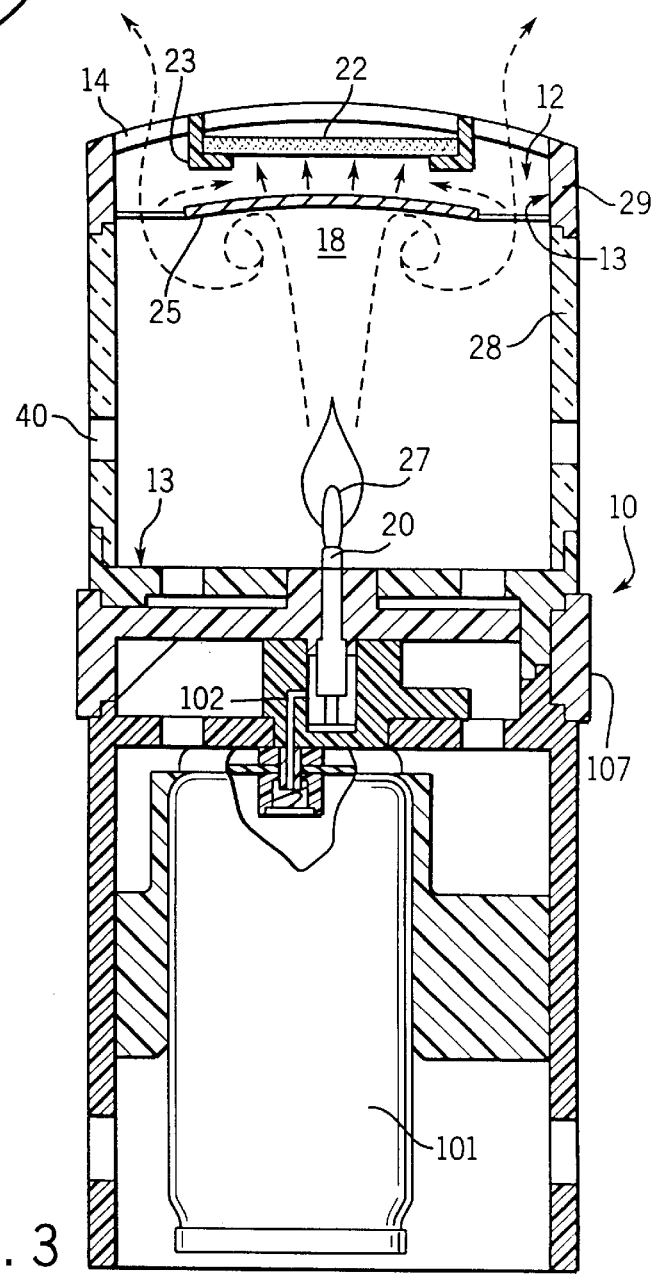
FIG. 3 is a vertical cross sectional view of the FIG. 1 embodiment.

We turn first to the embodiment of FIGS. 1–4. A dispenser, generally 10, encloses an internal heating chamber 12 having chamber side walls 13. There is also a chamber ceiling 14 that has exit vents 15.

The assembly includes a fuel burner 20. Fuel is supplied from a pressurized gas fuel source 101 through a fuel transfer route 102 by which fuel can be transferred to the fuel burner 20 in controlled amounts. Various types of valving and ignition systems can be used for this purpose (see e.g. U.S. Pat. No. 5,700,430).

Figure 4:
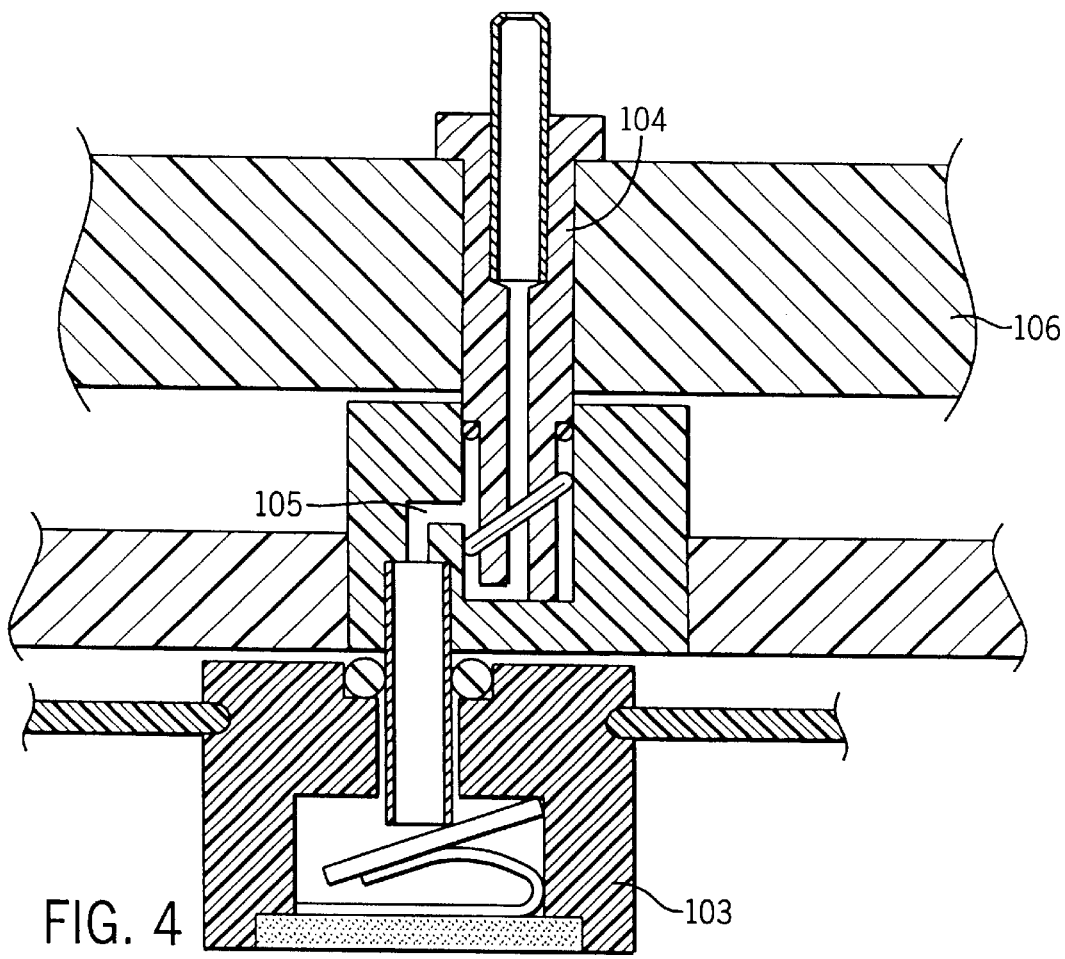
FIG. 4 is an enlarged cross sectional view of the shut-off valve portion of FIG. 3.

However, another option is depicted in FIGS. 1 and 4. Rotation of outer ring 107 will cause rotation of inner ring 106, thereby rotating a lower extension therefrom, which acts as a valve to control the amount of fuel being provided. Various known ignition systems, not shown, can be incorporated as well.

The dispenser also includes a cellulosic mat-like carrier 22, preferably impregnated with an insect control ingredient, preferably an insecticide. The carrier is slid through insert slot 41 in the outer housing and rests on carrier holder 23. The carrier holder 23 is located above the fuel burner and within the heating chamber 12.

The walls of the chamber provide an air-flow path to guide hot gases from the fuel burner 20 past the carrier holder 23 to heat the carrier 22. This provides the direct exposure of the volatile carrier to the gases created by the flame 27.

Preferably there is also a baffle 25 interposed between the fuel burner 20 and the carrier 22. This creates turbulence in the region 18 so as to better mix gases prior to their reaching the carrier 22. The baffle 25 also acts as a radiant heater beneath the carrier holder 23.

There is a light transmitting transparent or translucent plastic portion 28 which allows light from the flame 27 to be visible to a user of the dispenser. Thus, the dispenser both dispenses the volatile and provides a light function. In this form, the fuel burner 20 is preferably also within the heating chamber 12.

There may also be a cooling vent 40 that permits air outside of the heating chamber 12 to enter the heating chamber and partially cool the hot gases prior to their reaching the carrier. Vent 40 is located above the level of the fuel burner.

The carrier holder 23 is positioned within a part 29 of the heating chamber 12 that is visually obstructed in that it is either opaque or translucent such that the carrier holder is not clearly visible through the chamber side walls. It is preferred that the wall portions 28 and 29 be permanently assembled together (e.g. sonic welded) so that the heating chamber remains continuously enclosed.

Figure 5:
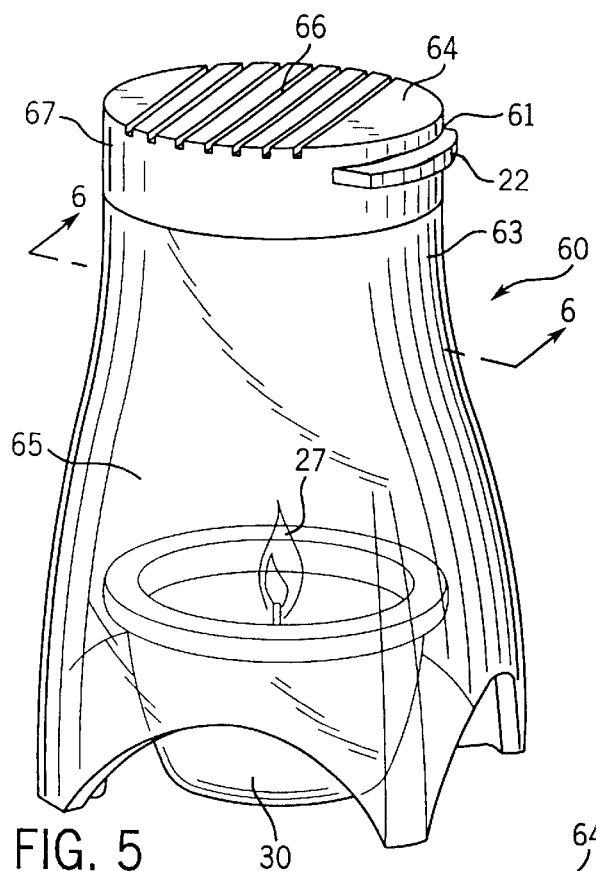
FIG. 5 is a perspective view of a second embodiment of the invention which uses a candle for fuel.
Figure 6:
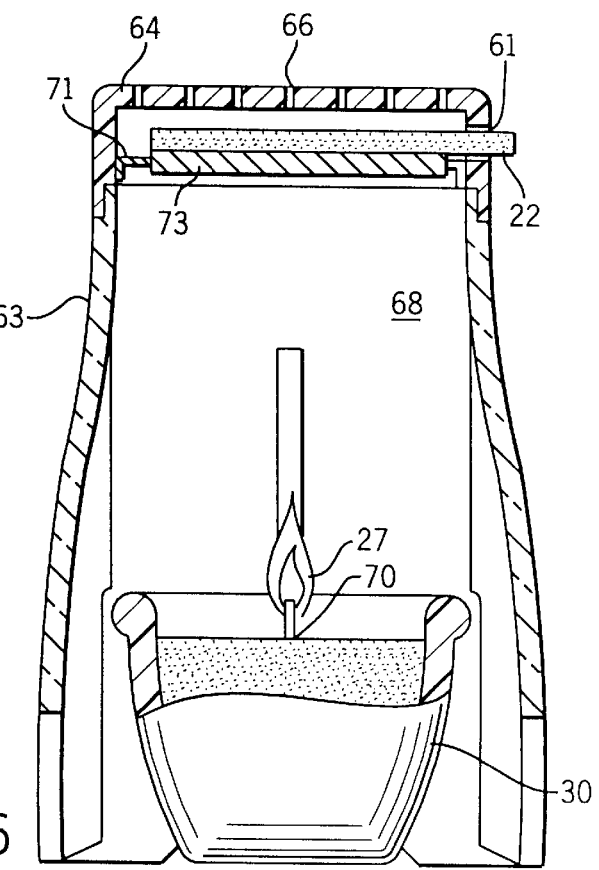
FIG. 6 is a cross sectional view of the embodiment of FIG. 5 taken along line 6—6 of FIG. 5.
Figure 7:
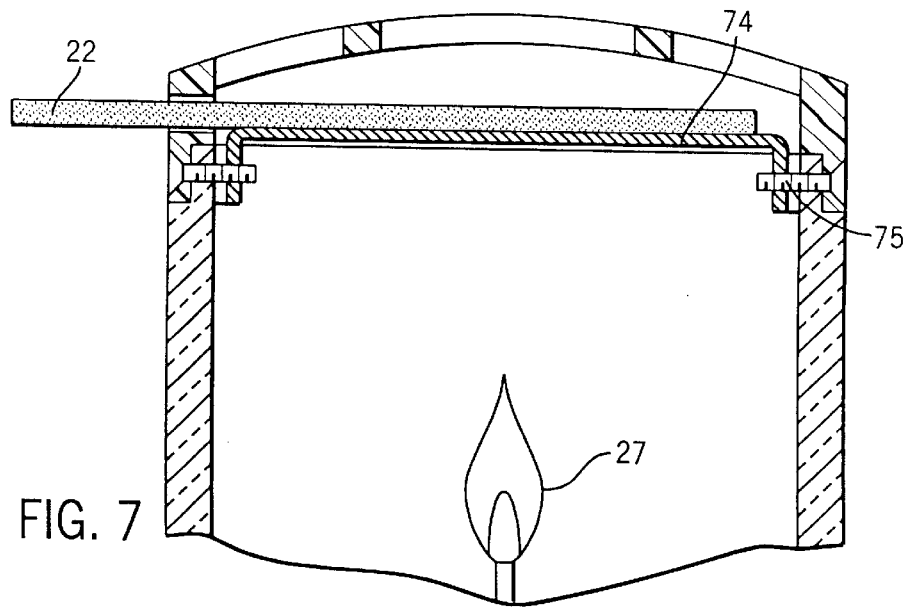
FIG. 7 is a cross sectional view of the upper portion of a heated volatile dispenser like that of FIG. 1 or FIG. 5, albeit showing an alternative carrier holder having a conductive sole plate.

Turning next to the embodiment of FIGS. 5–7 (generally 60), the fuel burner is now the wick of wax candle 30. There is a housing 65 with a cap 64 having vents 66. Side walls 63 help define the heating chamber. The volatile carrier 22 is inserted through slot 61 and in this case held on a sole plate 73 that is solid except for having spider leg radially peripheral attachments 71. The housing 65 can be lifted off the candle 30, the candle can be lit with a match, and the housing can be replaced to its FIG. 5 position.

In either case (the FIG. 1 or the FIG. 5 embodiment), the gases flow upward and ultimately around the volatile carrier before exiting. The gases will be sufficiently dispersed so as to provide desirable heating. The same flame which provides the heat source will also provide the light source.

Turning now to FIG. 7, another version of the sole plate 74 has its ends alternatively supported in side brackets 75. The design is otherwise similar to the embodiment of FIG. 5.

Figure 8:
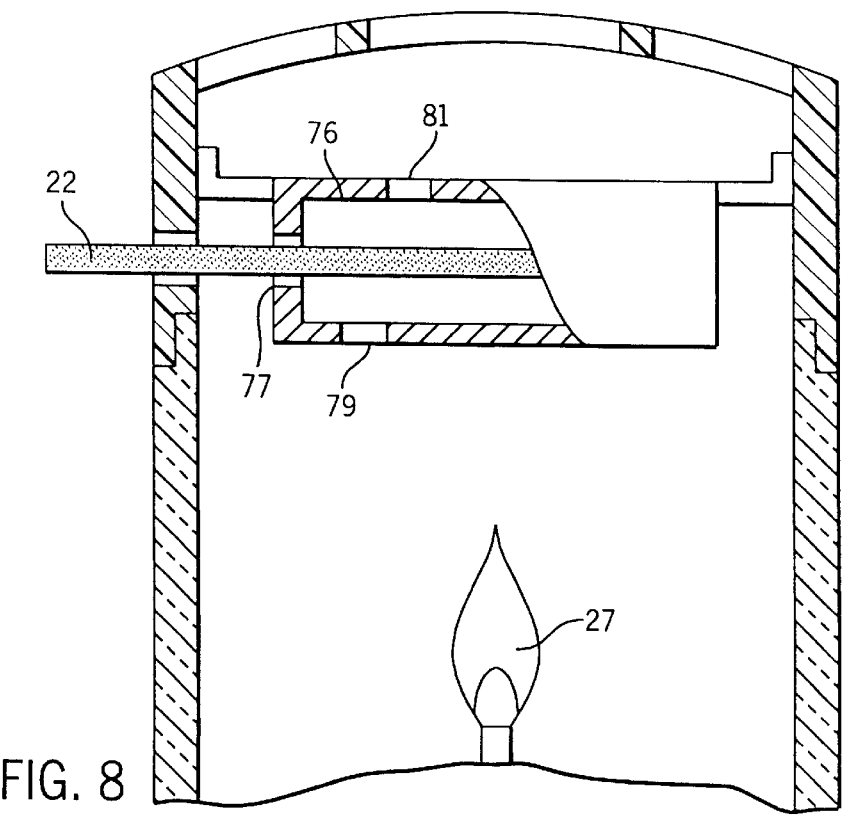
FIG. 8 is a cross sectional view of the upper portion of a heated volatile dispenser like that of FIG. 1 or FIG. 5, albeit showing another alternative volatile carrier holder in the form of an oven.

As shown in FIG. 8, there is provided an oven (generally 76). It has a side slot 77 that is aligned with the outer insert slot so as to permit the carrier 22 to be inserted not only through the outer insert slot, but also in the oven. In use, the oven 76 has a sufficient heat capacity that it serves to maintain a more constant temperature within the oven than might otherwise be experienced at that location in the flow of hot, gaseous gases if, for example, the heat source were a flickering flame. Bottom hole 79 permits gases to readily enter the oven. Top hole 81 permits them to readily exit.

Figure 9:
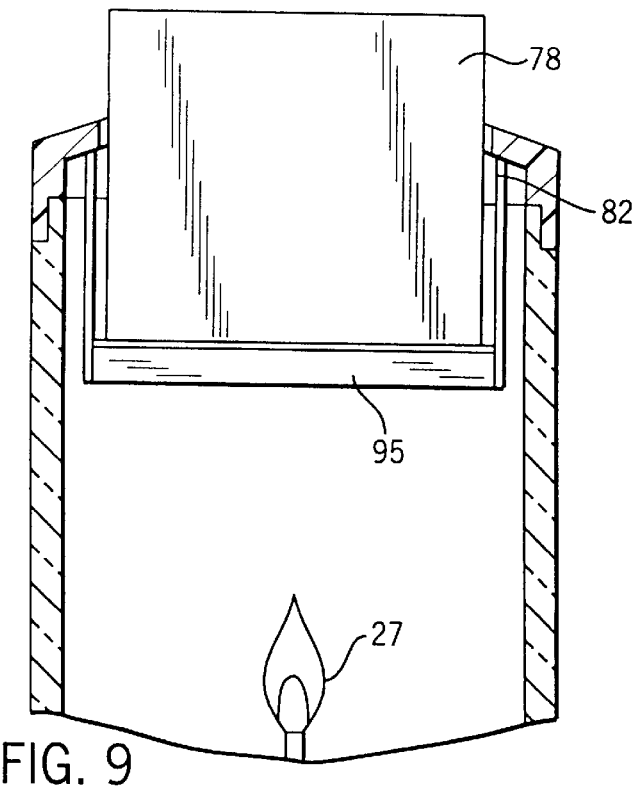
FIG. 9 is a cross sectional view of the upper portion of a heated volatile dispenser like that of FIG. 1 or FIG. 5, albeit showing another alternative volatile carrier holder that holds a volatile carrier in a vertical orientation.
Figure 10:
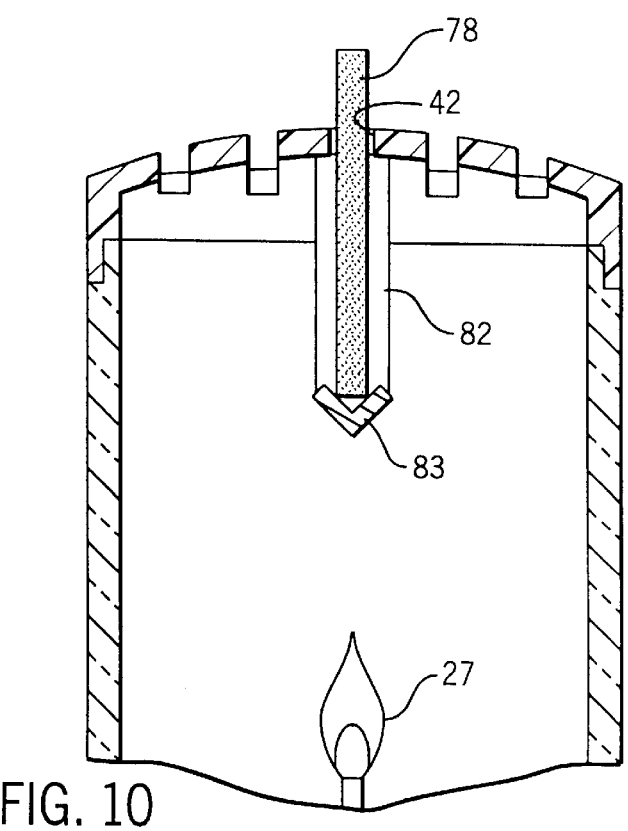
FIG. 10 is a partial cross sectional view of the heated volatile dispenser of FIG. 9, albeit taken at an angle which is rotated 90 degrees relative to that of FIG. 9.

FIGS. 9 and 10 depict the use of a generally vertically positioned carrier 78 inserted through an insert slot 42 and held by a carrier holder 82 having a protective guard 83 with side walls 95. This system has the advantage of exposing both sides of the carrier to roughly equivalent heat. The hot gas sweeps across the volatile-releasing surface in a direction generally parallel to the direction of linear extension of the volatile-releasing surfaces of the volatile carrier 22. Yet the downward edge of the volatile carrier is protected by protective guard 83 against undesirable overheating.

Figure 11:
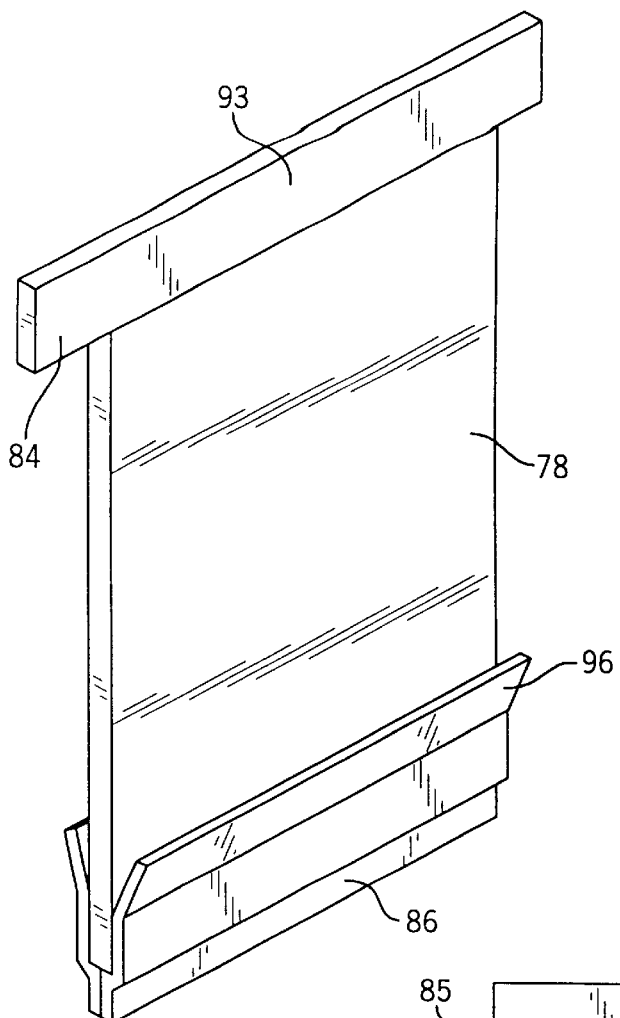
FIG. 11 is a perspective view of another volatile carrier of the invention having an edge guard.
Figure 12:
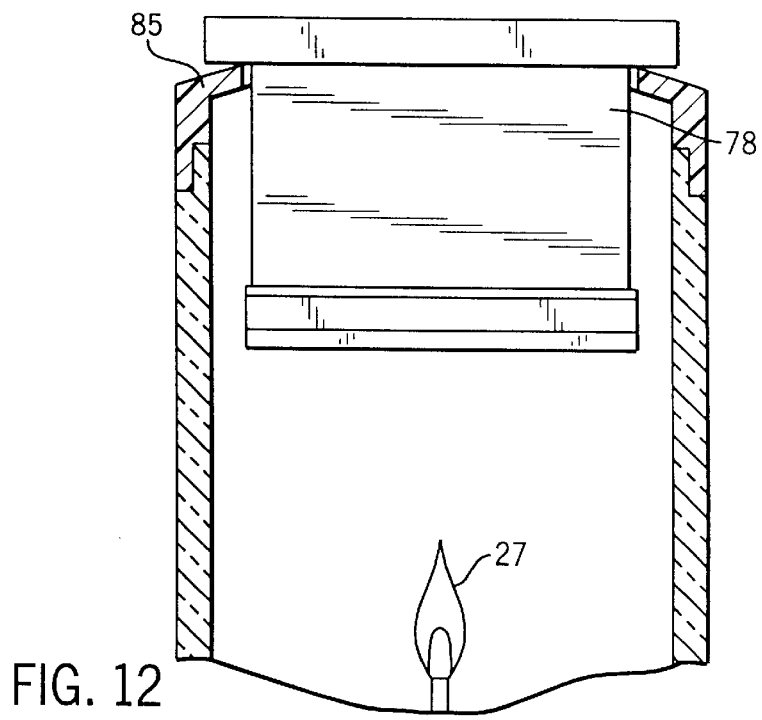
FIG. 12 is a cross sectional view generally corresponding to FIG. 9, but showing how surfaces of the heating chamber ceiling can serve as the carrier holder.

As shown in FIG. 11, the carrier 78 can be provided with a handle 93 and a heat resistant guard 86 positioned on a leading edge so as to be able to split the flow of hot gases when the carrier is held within the flow of hot gases. This again protects the treated section from edgeward impact of the hot gases. The guard preferably also has deflector vanes 96 extending sidewardly.

In these vertical forms, the carrier 78 is linearly extended and treated on both front and back sides.

Figure 15:
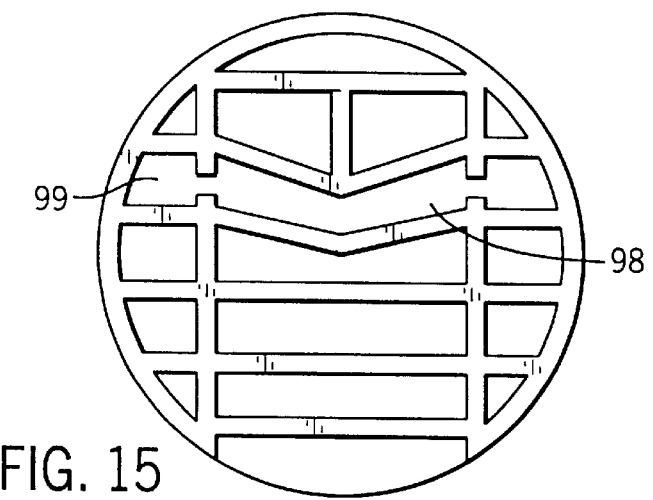
FIG. 15 is a top plan view of a dispenser having a ceiling with an insert slot suitable to receive the FIG. 13 volatile carrier.
Figure 13:
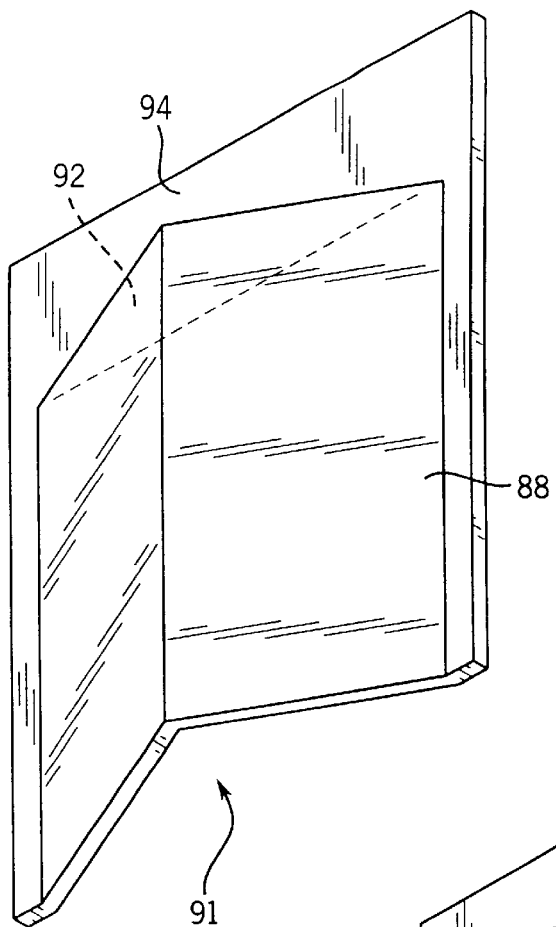
FIG. 13 is a lower frontal perspective view of a form of volatile carrier that can be used when the top of the FIG. 9 embodiment is provided with the FIG. 15 inlet slot.

As best seen in FIG. 15, an insert slot 98 that is not simply rectangular can be formed in the ceiling of the dispenser. When used with a carrier such as carrier 88 of FIG. 13, the edge 91 presents a non-interfering cross-sectional profile with respect to the insert slot 98, while still allowing some venting via exits 99. The opposite surface from surface 92 shown presents an interfering cross-sectional profile preventing the handle 94 from falling through the insert slot.

Figure 14:
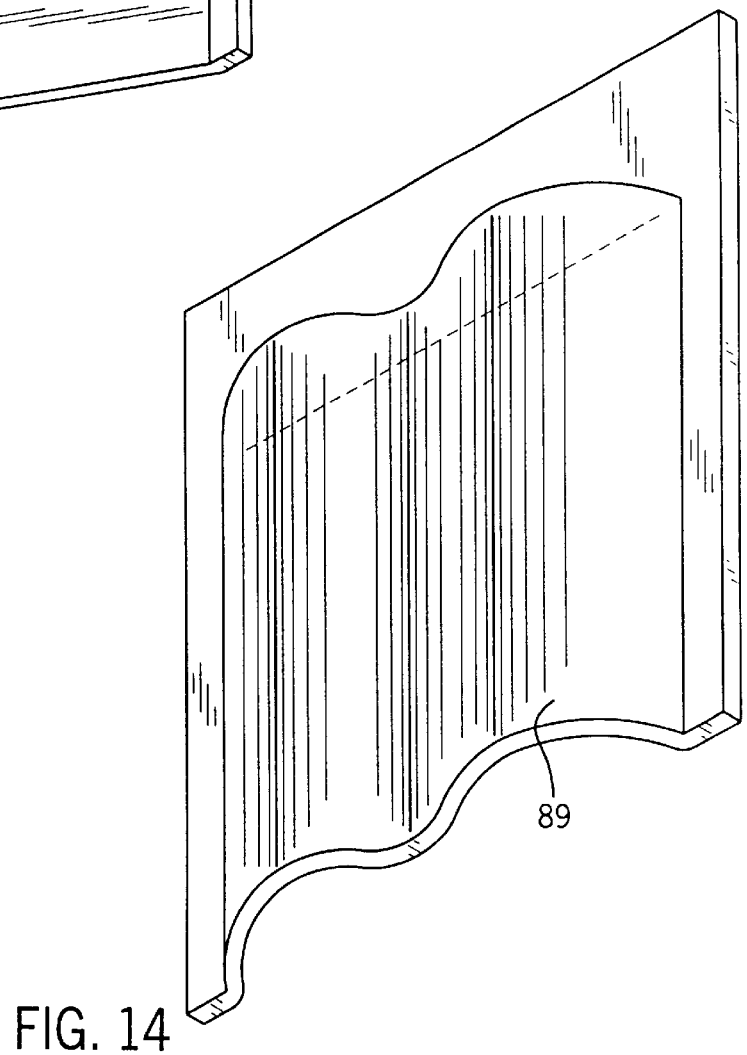
FIG. 14 is a lower frontal perspective view of another form of volatile carrier that can be used when the top of the FIG. 9 embodiment is provided with a wavy curve inlet slot.

If instead the carrier is carrier 89 as shown in FIG. 14, the FIG. 15 insert slot would then need to be a wavy line inlet. Thus, by using either form, the proper direction of the carrier can be controlled, and the public can be prevented from inserting mats into a given system that are not customized for use with that system.

In essence, this is a keying structure in which the cross-sectional profile of the insert slot must match with the cross-sectional profile of an inward end of the volatile carrier. The profile should depart from a rectangular slot, preferably using angularly intersecting and/or curved sections. Moreover, such a system is particularly useful in connection with horizontally extending carriers that have only one side treated with active.

Figure 16:
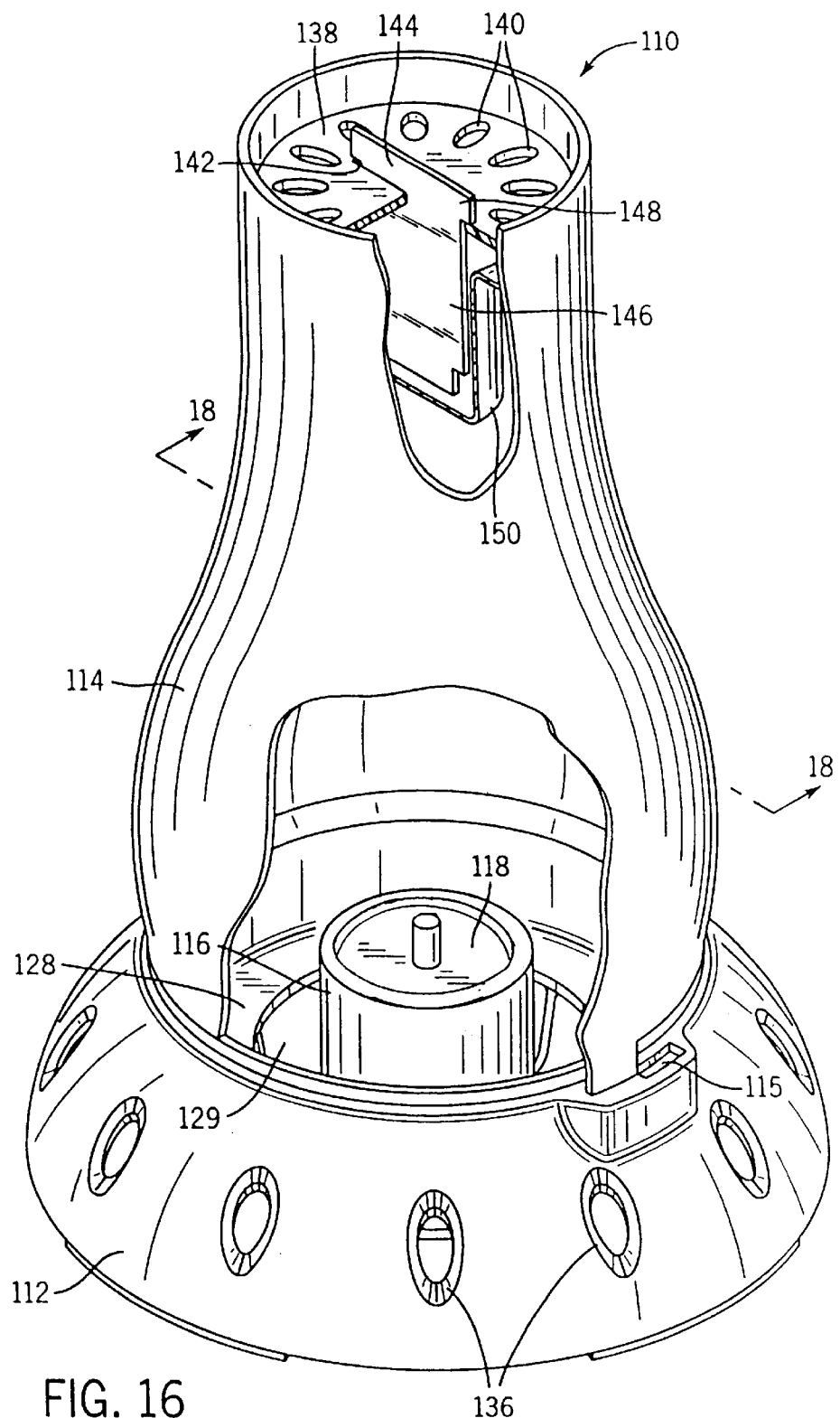
FIG. 16 is a perspective view of an alternative embodiment of the heated volatile dispenser of the invention, including a candle and a volatile carrier, with portions of the chimney broken away.
Figure 19:
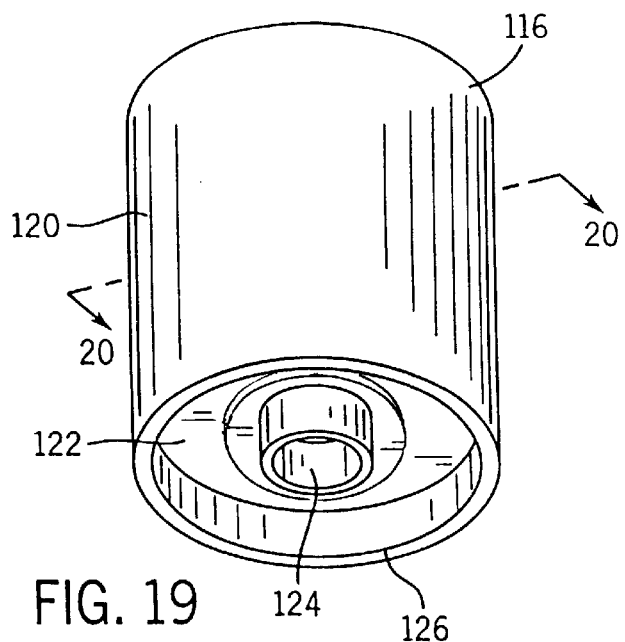
FIG. 19 is a perspective view from beneath of the candle of the invention.
Figure 20:
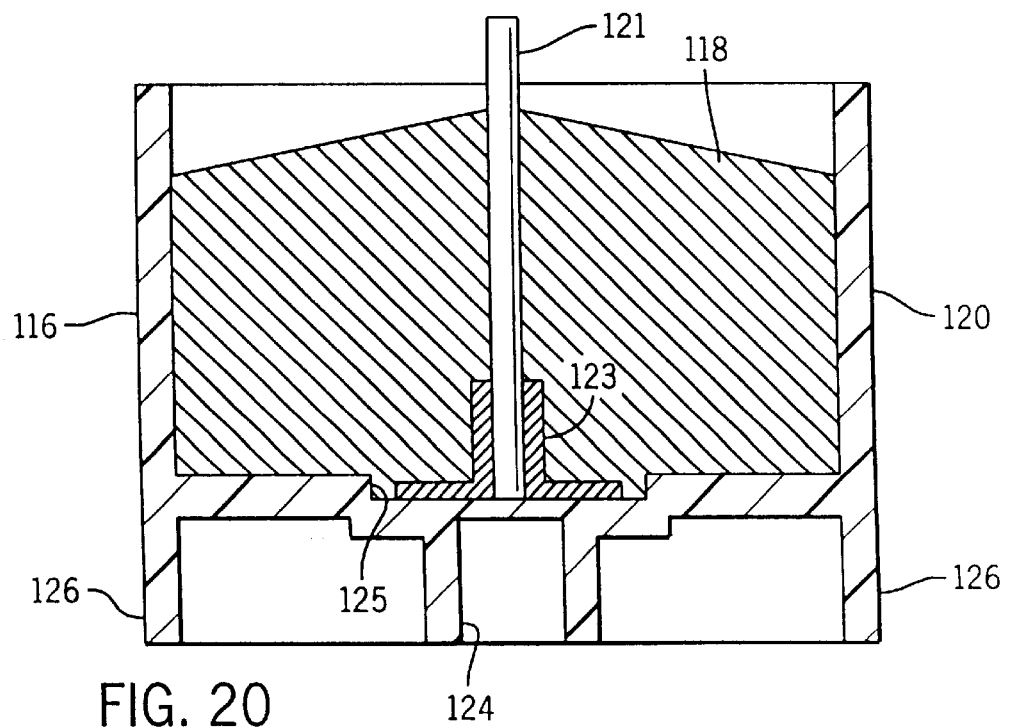
FIG. 20 is a cross sectional view of the candle of FIG. 19, taken along section lines 20—20 of FIG. 19.

An alternative and presently most preferred embodiment of the heated volatile dispenser of the invention is shown generally at in FIG. 16. The dispenser 110 has a base 112 that supports a removable chimney 114, the chimney attaching to the base with locking tabs 113 formed on the lower edge of the chimney that mate with locking slots 115 formed in the base. The chimney can be made of glass or, preferably, a heat-resistive clear or (preferably) translucent plastic. A fire-resistant polycarbonate is the preferred chimney material, such as the material sold as V-O flame rated polycarbonate, available under the name "Makrolon® 6455" from Bayer Corporation. The base 112 supports a candle cup 116 positioned centrally within the chimney 114. The features of the candle cup 116 are best shown in FIGS. 19 and 20.

The candle cup 116 is an open-topped, generally cylindrical cup that contains a wax candle 118. The candle cup 116 has cup walls 120 and a cup floor 122. Preferably the candle 118 has a wick 121 the bottom of which is held by a wick clip 123. Preferably the wick clip 123 is secured from slipping sidewardly on the cup floor 122. This can be accomplished in a variety of ways. For example, the wick clip 123 can simply be glued to the cup floor 122. Alternatively, a clip cup 125 can be formed as a central depression in the cup floor 122 having a diameter sized to receive the wick clip 123 but to restrain its sideways movement thereafter.

A centrally positioned, downwardly opening socket 124 extends downwardly from the underside of the cup floor 122. A cup support member 126 also extends downwardly from the cup floor 122 at least as far as the socket 124 extends and at locations remote from the socket. The cup support member 126 serves to facilitate manufacture and filling of the candle cup 116 by allowing the candle cup to sit upright on a conveyer belt or other surface without interference from the socket 124. The preferred cup support member 126 extends around the entire margin of the cup floor 122, as is best seen in FIG. 19. However, it will be appreciated by those skilled in the art that the cup support member need only be sufficiently remote from the socket and extend circumferentially sufficiently in one or more locations to provide a stable support such that the candle cup can sit on a flat surface without tipping. The candle cup 116 is made of a material sufficiently heat resistant as to be able to hold a burning candle therewithin without distorting or igniting. Once again, V-O flame rated polycarbonate is a preferred material.

Figure 17:
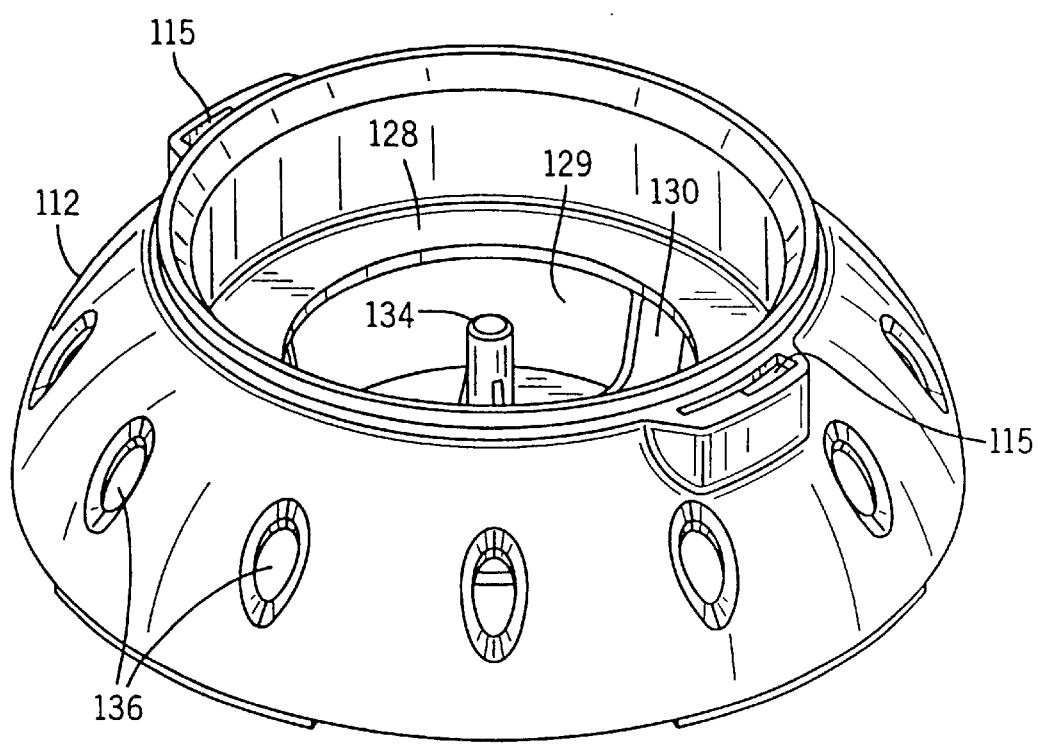
FIG. 17 is a perspective view of the base of the heated volatile dispenser of FIG. 16, with the chimney removed and without a candle.
Figure 18:
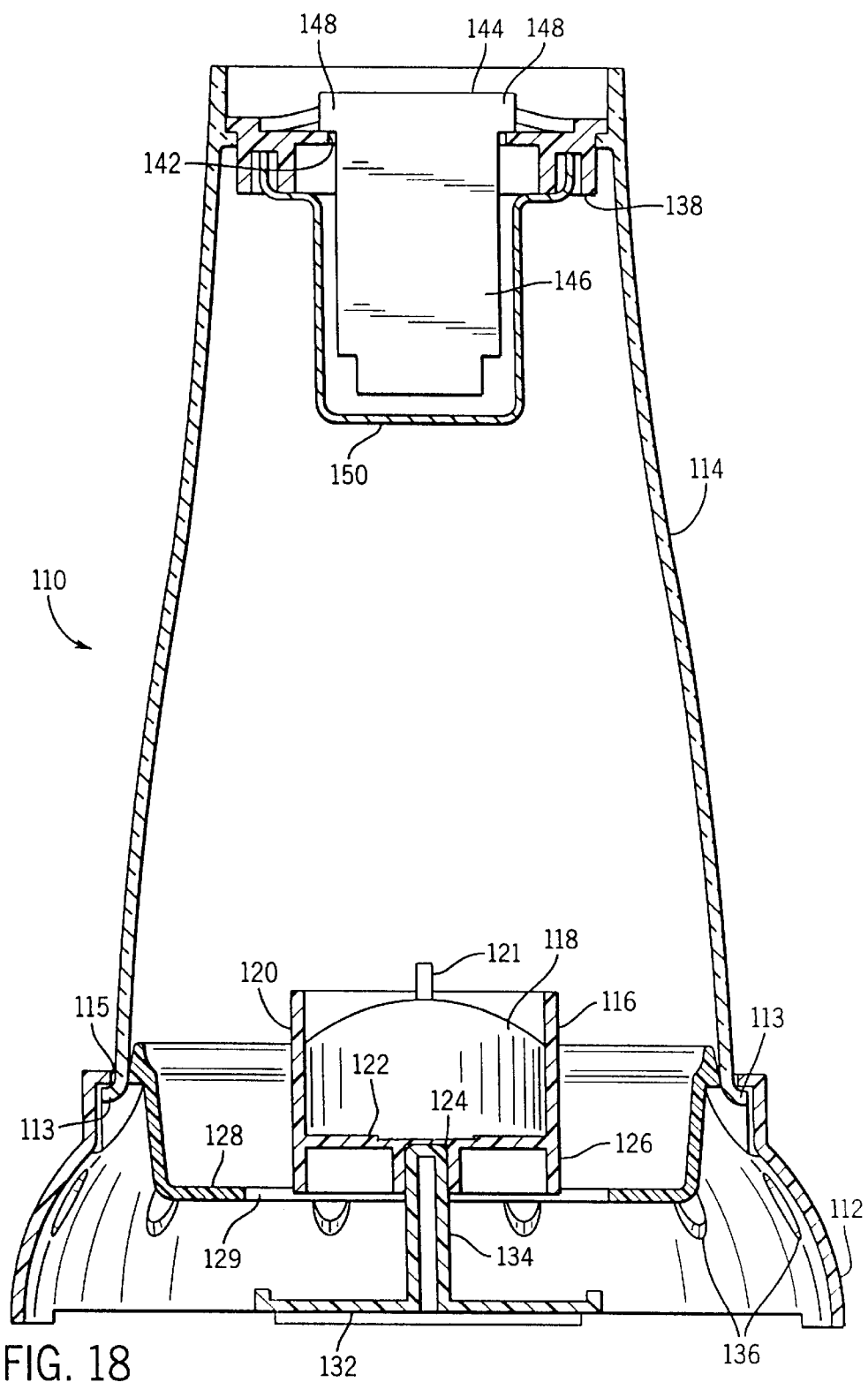
FIG. 18 is a cross sectional view of the heated volatile dispenser of FIG. 16, taken along sections lines 18—18 of FIG. 16.

As can be best seen in FIGS. 16–18, the base 112 has a base floor 128 that has a central ventilation opening 129 that is greater in diameter than the candle cup 116. Support elements 130 (seen in FIG. 16) extend downwardly from the underside of the base floor 128 and are attached to and support a wax catcher 132. The wax catcher 132 is a round, horizontally extending tray with low sides, the wax catcher having a diameter greater than that of the candle cup 116 so that any wax overflowing from the candle cup 116 lands on and is retained within the wax catcher. An attachment post 134 (seen in FIGS. 17 and 18) extends upwardly from the wax catcher and is sized to be received within the socket 124 of the candle cup 116 in firmly gripping relation. By this arrangement, the candle cup 116 is held within the central ventilation opening 129 with a circumferentially extending open space surrounding the candle cup walls 120.

The base 112 has ventilation holes 136 that communicate between the ambient air and the space beneath the base floor 128. When the candle 118 is lit and the chimney 114 is in place on the base 112, a convective air flow is generated that pulls air in through the ventilation holes 136, upward under the candle cup 116 and through the open space of the ventilation opening 129 surrounding the candle cup walls 120, and on up the chimney. As a consequence, the candle 118 is ventilated from below the level of the candle cup, and consequently the candle cup floor 122 and walls 120 are cooled by the air flow. Furthermore, a sheath of cooler air appears to form, flowing upwardly within the chimney 114, surrounding the upward, centrally located flow of hot gases generated by the lit candle 118 and, in fact, tending to cause the hot gases to form a focused central area within the overall air flow that is hotter than the more stirred mix of gases and air experienced in a device otherwise similar but with air vents only at the periphery of the base floor 128. This pattern of air flow maintains both the candle cup 116 and the walls of the chimney 114 at a cooler temperature, while focusing a higher heat at the center of the area contained within the upper part of the chimney. This cooling effect helps to preserve the candle cup 116 and chimney 114 and make the chimney cooler to the touch while simultaneously establishing a hot area for driving off volatile material loaded on a substrate held in that area.

A ceiling 138 is positioned within the chimney 114 at its upper end. The ceiling 138 has ceiling vents 140 and an insert slot 142 that communicate between the interior of the chimney 114 and the outside air above the chimney. Hot gases flowing upwardly from the burning candle 118 can escape the chimney 114 through the ceiling vents 140. The insert slot 142 is sized to receive a volatile carrier, such as the mat 144 shown in FIG. 16 and following. The preferred mat 144 is flat, having a linearly extended volatile bearing section 146 with sidewardly extending ears 148. The volatile bearing section 146 of the mat 144 is made small enough to be inserted from above into the insert slot 142, while the ears 148 are made too wide to slip through the insert slot. By this arrangement, the volatile bearing section 146 can be suspended within the chimney 114, with the mat 144 hanging by the ears 148, the insert slot 142 and upper surfaces of the ceiling 138 serving as a carrier holder, holding the volatile carrier—the mat 144—in a portion of the heating chamber that can be translucent, thus being a location that is visually obstructed.

A baffle strip 150, made of a heat-resistive material such as metal, is fastened to the under side of the ceiling 138, the baffle strip extending down one side of the volatile bearing section 146 of a mat 144 held beneath the ceiling, then sideways under the entire width of the volatile bearing section, and finally upwardly along the other side of the volatile bearing section. The baffle strip 150 serves to mix the flow of hot gases rising above the candle 118 and to protect the downwardly facing edge of the volatile bearing section 146 from the direct impact of the hottest gases rising from the candle.

The interior of the chimney 114 provides a heating chamber whose walls are defined by the sidewalls of the chimney. This heating chamber is vented to the outside air via the ceiling vents 140. The candle cup 116 provides a fuel burner with the candle 118 being its fuel source. The interior of the chimney 114 defines an air-flow path that guides the hot gases from the fuel burner past the mat 144, which is the volatile carrier of the device, to heat the mat by directly exposing it to the hot gases prior to their escape from the heating chamber into the surrounding air. The baffle strip 150 provides a baffle similar to the baffles described above in alternative embodiments of the heated volatile dispenser of the invention.

Figure 21:
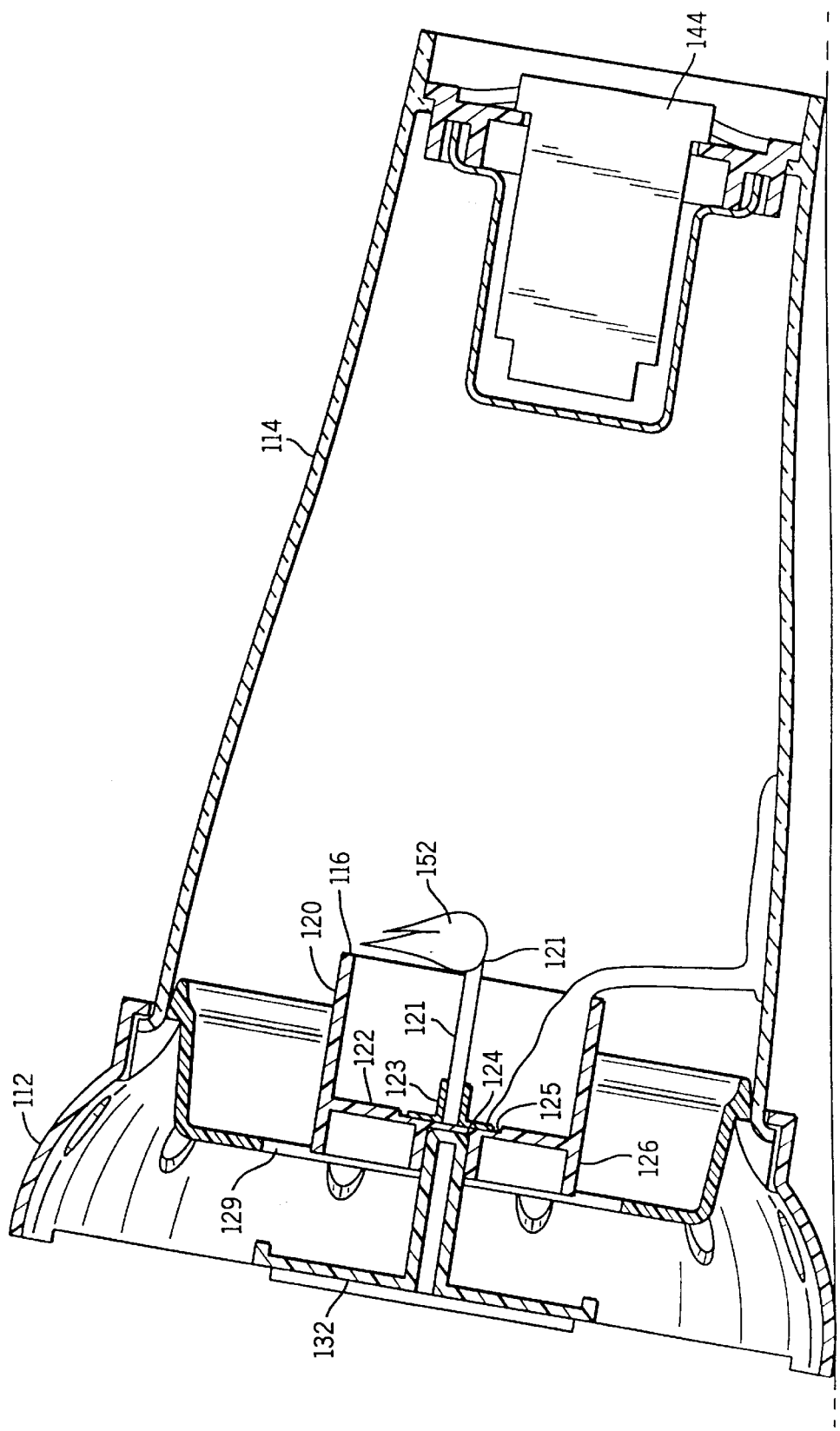
FIG. 21 is a cross sectional view corresponding to that of FIG. 18 but with the heated volatile dispenser shown tipped on its side on a supporting surface.

Preferably, the embodiment of the heated volatile dispenser shown generally at 110 is adapted to cause its candle 118 to self-extinguish if the dispenser tips over. The attachment post 134 is sized to be firmly gripped by the socket 124 when the candle cup 116 is installed in the base 112 to the extent necessary to retain the candle cup in place should the dispenser 110 tip over on its side, as is shown in FIG. 21. If the candle 118 is burning when the dispenser 110 tips over, any molten candle wax immediately drains from the now sidewardly opening candle cup 116. The flame 152 at the wick 121 continues to melt any remaining wax, which also drains from the candle cup 116, until the level of the wax has been so reduced as to no longer feed the wick. At that point, the flame 152 extinguishes. Although FIG. 20 illustrates a situation in which the candle cup 116 is sufficiently tipped as to be presented downwardly from the horizontal, the flame 152 will self-extinguish when tipped at any angle sufficient to allow molten wax to drain down to the level that the wick 121 becomes starved for fuel.

Figure 22:
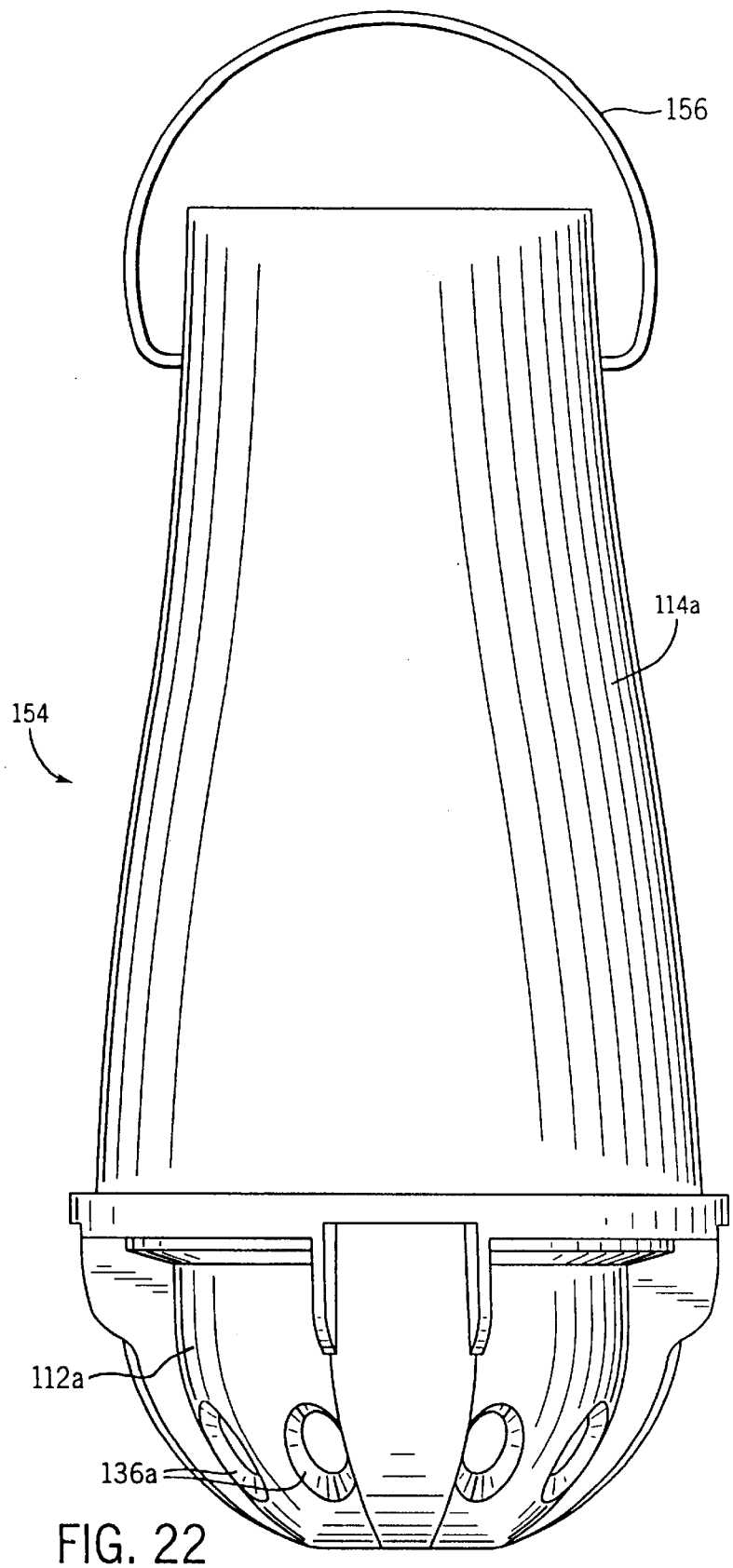
FIG. 22 is a side elevation view of an alternative embodiment of the heated volatile dispenser of the invention.
Figure 23:
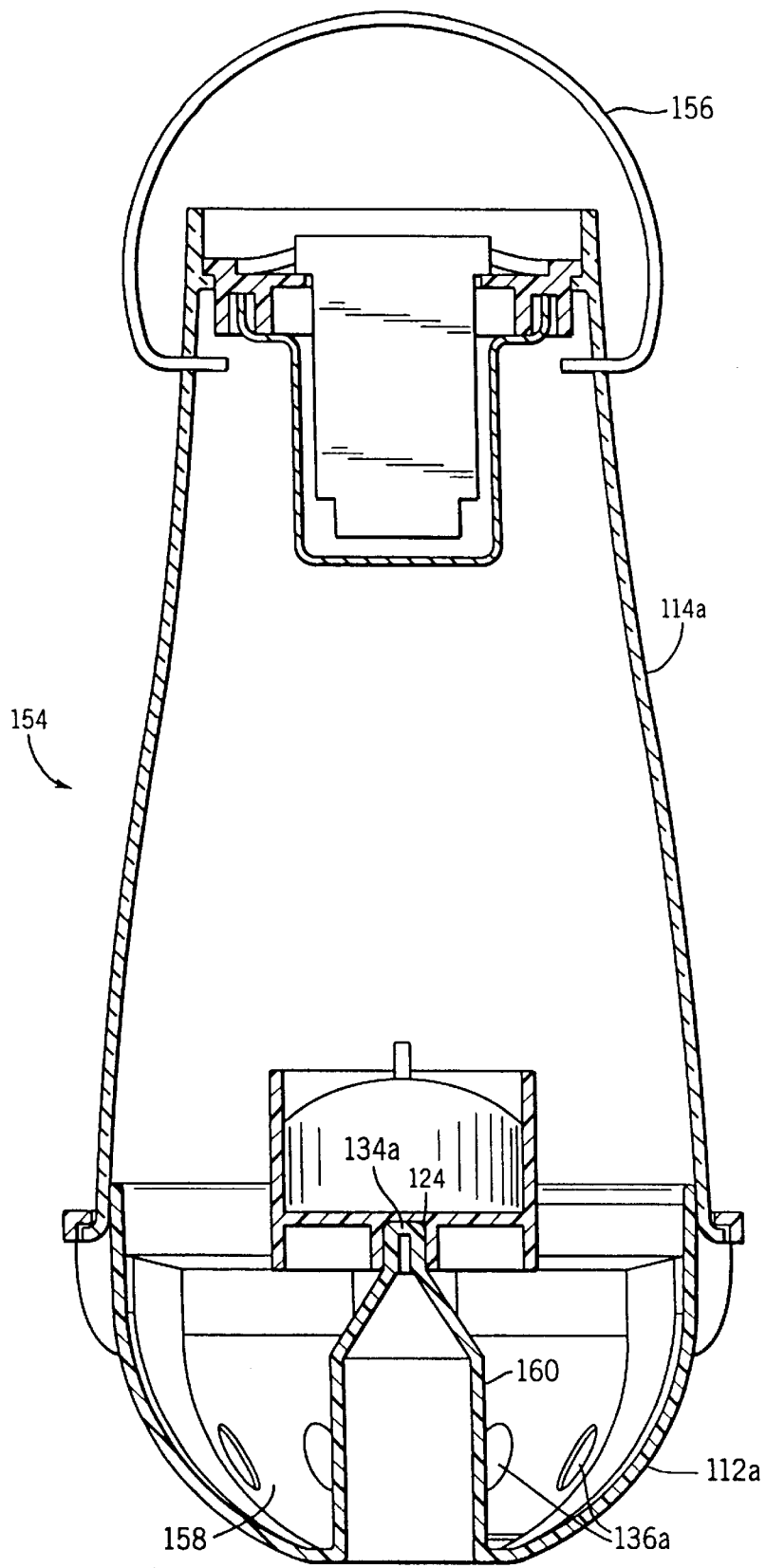
FIG. 23 is a cross sectional view of the heated volatile dispenser of FIG. 22, the view otherwise generally corresponding to the view of FIG. 18.

FIG. 22 is side elevational view (and FIG. 23 is a cross sectional view) of an alternative embodiment of the heated volatile dispenser of the invention, shown generally at 154. Volatile dispenser 154 is a modified form of the heated volatile dispenser 110 of FIG. 16. All parts of volatile dispenser 154 that directly correspond to parts of the volatile dispenser 110 are identified by the same reference numbers with the addition of the letter "a", without further discussion.

The volatile dispenser 154 differs from the volatile dispenser 110 in that dispenser 154 is designed to be hung from a hook or other overhead support (not shown). A hanger 156 capable of hanging from such a hook is attached to the upper part of the chimney 114a, preferably in freely turning relation to the chimney so that the weight of the dispenser 154 causes it to hang directly downwardly from the hook or other overhead support. This arrangement allows dispenser 154 to function generally in the same way as does dispenser 110 when dispenser 110 is resting on a horizontal surface.

The other differences between dispensers 154 and 110 all reside in the base 112a. The base 112a has a floor 158 that is downwardly curved at its center so as to discourage the use of dispenser 154 except by being hung.

The base 112a has an attachment post 134a that is sized to be received within the socket 124 of a candle cup 116. The attachment post 134a is located at the top of a central pedestal 160 that rises from the floor 158. When a candle cup 116 is mounted on the attachment post 134a, it is importantly advantageous for the cup walls 120 and cup floor 122 to be freely ventilated. Therefore, preferably the diameter of the central pedestal 160 is less than that of such a candle cup 116 for a distance beneath the bottom of the candle cup sufficient to allow for such ventilation. Preferably, the top of the pedestal 160 is an upwardly pointing cone or comparable, upwardly diminishing shape that terminates in the attachment post 134a, as is shown in FIG. 23. Also preferably, the central pedestal 160 is hollow and opens downwardly from the base 112a, allowing the dispenser 154 to be alternatively mounted on a stake or post (not shown) inserted into the central pedestal from beneath.

Base ventilation holes 136a are spaced around the base 112a at a level beneath that of the cup floor 122 of a candle cup 116 when it is mounted on the attachment post 134a.

The base ventilation holes 126a communicate between the ambient air and the interior of the base. Thus, as in the dispenser 110, a candle cup 116 mounted on the attachment post 134a is held within a circumferentially extending open space. As in the dispenser 110, when a candle 118 is lit and the chimney 114a is in place on the base 112a, a convective air flow is generated that pulls air in through the ventilation holes 136a, upward under the candle cup 116 and through the open space surrounding the candle cup walls 120, and on up the chimney. As a consequence, the candle 118 is ventilated from below the level of the candle cup 116. Consequently the candle cup floor 122 and walls 120 are cooled, and the beneficial pattern of air flow discussed above with respect to the dispenser 110 is established.

A preferred embodiment of the kit of the invention, as disclosed above, includes at least one candle as a fuel source and at least one volatile carrier. The preferred candle is a candle 118, as already described, contained within a candle cup 116, and is made of paraffin wax with a preferred weight of from 15 to 20 grams and an especially preferred weight of from 16 to 17 grams. Ideally, the candle is made by the process of bonding small wax granules by simply forcefully pressing them in a compression mold. The technique is well known in the candle making art and produces candles of consistent dimensions and densities. The preferred candle, whether made by that or any other method, has a diameter of about 37 mm and an overall height at the candle's center of about 20 mm, the height tapering down to about 15 mm at the circumference of the candle. A candle of this size will burn for about 4 hours.

The preferred volatile carrier for the kit when used with the candle just described is made of conventional, fibrous mosquito mat material and preferably of a cellulosic, felted pulp mat material. The preferred mat weighs approximately 1 gram before being treated with an insect control material, including the standard 5 to 7% moisture absorbed by such materials. Each such mat is treated with approximately 375 mg of d-cis/trans allethrin (or about 22% by weight of the mat) as a volatile insect control active ingredient. The heat from the preferred candle just described is sufficient to exhaust the d-cis/trans allethrin from the mat by the time the candle has been consumed, when the mat is positioned edge-on at approximately 9.5 cm above the candle in a location free of side drafts, such as is found within the heated volatile dispenser shown in FIG. 16 and following. The term "exhaust" has the meaning previously defined.

The various parts of the dispenser described above can be manufactured by conventional means from heat-resistant plastics, metal, glass, and the like. The volatile carriers disclosed can be made using conventional methods and materials well known in the art, such as those used for making conventional mosquito mats, volatile gel carriers, volatile-containing polymers, and the like.

The preceding description is merely of preferred embodiments of the invention. One skilled in the art will readily apprehend alternative embodiments that nevertheless fall within the scope and breadth of the invention. Thus, the claims should be looked to in order to understand the full scope of the invention.

INDUSTRIAL APPLICABILITY

Heated volatile dispensers and volatile carriers, and methods of using them, are described. They are useful in the practical control of insects and other pests and in air scenting.

What is claimed is:

1. A heated volatile dispenser for dispensing volatile materials from a volatile carrier, the dispenser comprising:
   a. an enclosed heating chamber capable of holding a volatile carrier therewithin, the heating chamber having chamber walls and being vented to the outside air;
   b. a fuel burner; and
   c. an air-flow path to guide hot gases generated by the fuel burner past a volatile carrier held within the heating chamber to heat the volatile carrier by the direct exposure of the volatile carrier to the hot gases, the air-flow path then directing the hot gases to escape from the dispenser to the outside air.

2. The heated volatile dispenser of claim 1 wherein the enclosed heating chamber has a ceiling and an exit vent in at least one of the chamber walls and ceiling, the exit vent communicating between the interior of the heating chamber and the outside air; and wherein the air-flow path first guides hot gases from the fuel burner past the volatile carrier and then directs the hot gases through the exit vents to escape from the dispenser.

3. The heated volatile dispenser of claim 1 further comprising a baffle, interposed between the fuel burner and the location where a volatile carrier can be held, to create turbulence that mixes hot gases from the fuel burner prior to their reaching a volatile carrier held within the dispenser.

4. The heated volatile dispenser of claim 3 wherein the location where a volatile carrier can be held is spaced above the baffle and the baffle is so located as to be heated by hot gases contacting the baffle from below, the hot baffle serving as a radiant heater beneath a volatile carrier held within the dispenser.

5. The heated volatile dispenser of claim 1 wherein the fuel burner supports a flame positioned within the heating chamber and the heating chamber walls include a light-transmitting portion that allows light from the flame to be visible to a user of the dispenser through the light-transmitting portion.

6. The heated volatile dispenser of claim 5 wherein a. the walls of a part of the heating chamber are selected from the group consisting of opaque and translucent so as to be visually obstructed, and b. the location at which a volatile carrier is held within the heating chamber is within the visually obstructed part of the heating chamber.

7. The heated volatile dispenser of claim 1 including a carrier holder positioned to receive and hold a volatile carrier in a location above the fuel burner and contained within the heating chamber.

8. The heated volatile dispenser of claim 7 wherein the carrier holder comprises a heat-conductive sole plate that supports the volatile carrier.

9. The heated volatile dispenser of claim 7 wherein an insert slot communicates between the interior of the heating chamber and the exterior of the heated volatile dispenser, through which insert slot a volatile-bearing volatile carrier can be inserted to be held by the carrier holder.

10. The heated volatile dispenser of claim 9 wherein the insert slot includes keying structures that impart a cross-sectional profile to the insert slot that so restricts access thereto as to prevent the insertion through the slot of any volatile carrier not capable of presenting a non-interfering cross-sectional profile to the cross-sectional profile of the insert slot.

11. The heated volatile dispenser of claim 10 wherein the keying structures define a cross-sectional profile selected from the group consisting of angularly intersecting and curved sections.

12. The heated volatile dispenser of claim 9 wherein the heating chamber has a ceiling and the insert slot extends through the ceiling.

13. The heated volatile dispenser of claim 9 wherein the volatile carrier includes a treated section loaded with the volatile material to be dispensed and a handle, and wherein the keying structures of the insert slot present an interfering cross-sectional profile with respect to a portion of the handle.

14. The heated volatile dispenser of claim 7, wherein the carrier holder is in the form of an oven located within the heating chamber, the oven having oven walls and being positioned within the air-flow path so as to be heated by hot gases rising from the fuel burner, the oven having openings sufficient to admit hot gases rising from the fuel burner and having vents to allow the escape therefrom of volatile materials.

15. The heated volatile dispenser of claim 1 wherein the fuel burner burns fuel selected from the group consisting of a candle, a burnable solid, a pressurized gas, a combustible liquid, and a gelled combustible liquid.

16. The heated volatile dispenser of claim 1, wherein the fuel burner is ventilated from beneath via circumferentially extending open space surrounding the fuel burner, which space is vented to the ambient air.

17. The heated volatile dispenser of claim 1 including a base located beneath the heating chamber, the base having a ventilation opening through which ambient air can pass to continue upwardly through the heating chamber, and wherein the fuel burner is so supported by the base in relation to the ventilation opening that the fuel burner is circumferentially ventilated from beneath.

18. The heated volatile dispenser of claim 17 wherein the fuel burner employs a candle.

19. The heated volatile dispenser of claim 17 wherein the fuel burner includes a candle cup having cup walls and a downwardly opening socket, and the base includes an attachment post to engage the socket and thus hold the candle cup.

20. The heated volatile dispenser of claim 17 wherein the heating chamber includes a light-transmitting chimney attached to the base.

21. The heated volatile dispenser of claim 17 including a hanger by which the dispenser may be suspended from above.

22. The heated volatile dispenser of claim 21 wherein the underside of the base is so shaped as to prevent the dispenser being supported in an upright orientation on a flat surface.

23. The heated volatile dispenser of claim 1 wherein a. the fuel burner includes a candle contained within a candle cup, the candle cup having a floor and upright walls terminating in an open top and being made of a heat resistant material, and b. the candle cup is fixedly positioned within the heating chamber, so that, should the volatile dispenser tip sidewardly while the candle is burning, the candle's heat contained within the candle cup will melt at least a portion of the candle's wax, allowing it to flow from the open top to starve the candle's wick of fuel, causing the candle to self-extinguish.

24. A volatile carrier suitable for use with a heated volatile dispenser that has an insert slot through which the volatile carrier can be inserted to load the heated volatile dispenser, the insert slot having keying structures that impart to it a cross-sectional profile that departs at least in part from a rectangular opening and that so restricts access thereto as to prevent loading through the slot any volatile carrier not having a non-interfering cross-sectional profile to the insert slot, the volatile carrier comprising a treated section bearing the volatile material to be dispensed and having a cross-sectional profile that is non-interfering with respect to the insert slot.

25. The volatile carrier of claim 24 wherein the non-interfering cross-sectional profile of the treated section is selected from the group consisting of angularly intersecting and curved sections.

26. A volatile carrier suitable for use with a heated volatile dispenser designed to expose a volatile carrier to a flow of hot gases, the volatile carrier comprising
   a. a treated section that is linearly extended and is loaded with the volatile material to be dispensed, the treated section having front and back sides and a leading edge; and
   b. a heat-resistant edge guard positioned on the leading edge to split the flow of hot gases when the volatile carrier is held within a flow of hot gases with the leading edge presented toward the hot gas flow to direct the hot gases over both the front and back sides, and to assist in protecting the treated section from direct, edgeward impact from the hot gases.

27. The volatile carrier of claim 26 wherein the edge guard has deflector vanes extending sidewardly with respect to the direction of linear extension of the treated section.

28. A method for dispensing ingredients volatilizable by application of heat, the method comprising the steps of:
   a. providing a heated volatile dispenser having:
      i. an enclosed heating chamber capable of holding a volatile carrier therewithin, the heating chamber having chamber walls and being vented to the outside air;
      ii. a fuel burner; and
      iii. an air-flow path to guide hot gases from the fuel burner past a volatile carrier held within the heating chamber to heat the volatile carrier by the direct exposure of the volatile carrier to the hot gases, the air-flow path then directing the hot gases to escape from the dispenser to the outside air;
   b. positioning a volatile carrier loaded with ingredients to be volatilized in the flow of hot gases;
   c. igniting fuel at the fuel burner; and
   d. allowing the volatile carrier to be heated and the ingredients thus volatilized therefrom to be vented from the dispenser.

29. A heated volatile dispenser for use with a volatile carrier having a volatile-loaded section having a linearly extended, volatile-releasing surface, the heated volatile dispenser comprising:
   a. a fuel burner generating upwardly flowing hot gases; and
   b. a carrier holder that can hold the volatile carrier with the volatile-loaded section above the fuel burner and within the hot gases in an orientation such that hot gas sweeps across the volatile-releasing surface.

30. The heated volatile dispenser of claim 29 wherein the carrier holder can hold the volatile carrier in an orientation such that hot gas sweeps across the volatile-releasing surface in a generally vertical direction generally parallel to the direction of linear extension of the volatile-releasing surface to release volatile therefrom.

31. The heated volatile dispenser of claim 29 for use with a volatile carrier having at least two volatile-releasing surfaces and wherein the carrier holder can hold the volatile carrier in an orientation such that hot gas sweeps across at least two of the volatile-releasing surfaces at the same time.

32. The heated volatile dispenser of claim 29 further comprising:
   a. a heating chamber within which the carrier holder positions the volatile carrier, the heating chamber having chamber walls, a ceiling, and exit vents in at least one of the chamber walls and ceiling, the exit vents communicating between the interior of the heating chamber and the outside air; and
   b. an air-flow path to guide hot gases from the fuel burner to directly contact the volatile-releasing surface of the volatile carrier, the hot gases then being vented from the dispenser.

33. The heated volatile dispenser of claim 29 for use with a volatile carrier having a linearly extended, volatile treated section having a leading edge to be presented toward the flow of hot gases, the carrier holder including a heat resistant edge guard suitable to extend along the leading edge of a volatile carrier when the volatile carrier is held in the carrier holder.

34. The heated volatile dispenser of claim 29 further comprising a baffle interposed between the fuel burner and the carrier holder to create turbulence that mixes hot gases from the fuel burner prior to their reaching the carrier holder.

35. The heated volatile dispenser of claim 29 wherein the fuel burner supports a flame located within the heating chamber and the heating chamber walls include a light-transmitting portion that allows light from the flame to be visible to a user of the dispenser.

36. The heated volatile dispenser of claim 29 wherein
   a. the walls of a part of the heating chamber are selected from the group consisting of opaque and translucent; and
   b. the carrier holder is positioned within that part of the heating chamber so that the carrier is not visible through the chamber walls.

37. The heated volatile dispenser of claim 29 wherein an insert slot communicates between the heating chamber and the exterior of the heated volatile dispenser, extending through one of the ceiling or the chamber walls, through which insert slot a volatile-bearing volatile carrier may be inserted to be held by the carrier holder.

38. The heated volatile dispenser of claim 29 wherein the fuel burner is selected from the group consisting of a candle, a solidified combustible liquid, a burnable solid, a catalytic heater, a pressurized gas burner, and a wick that is fueled with a combustible liquid.

39. A method of dispensing a volatile material from a volatile carrier having a volatile-loaded section having a linearly extended, volatile-releasing surface, the method comprising the steps of:
   a. providing a fuel burner generating a flow of hot gases; and
   b. holding the volatile carrier with the volatile-loaded section within the flow of hot gases in an orientation such that hot gas sweeps across the volatile-releasing surface, in contact therewith.

40. The method of claim 39 wherein the volatile-releasing surface is held essentially vertical.

41. The method of claim 39 wherein the volatile carrier has both front and back volatile-releasing surfaces and the step of holding the volatile carrier within the hot gases includes holding the volatile carrier in an orientation such that hot gas sweeps across both the front and back volatile releasing surfaces at the same time.

42. A method of dispensing a volatile material from a volatile carrier by use of a heated volatile dispenser of the sort that utilizes a fuel burner to generate a flow of hot gases over the volatile carrier to release volatile material therefrom, the method comprising the steps of:

a. providing a fuel source for the fuel burner having an amount of fuel selected to become exhausted and cause the fuel burner to extinguish at the same time that the volatile of the volatile carrier is substantially exhausted so that the extinguishing of the fuel burner is a use-up cue for the substantial exhaustion of volatile from the volatile carrier; and b. lighting the fuel burner.

43. The method of claim 42 wherein the heated volatile dispenser used is of the sort in which fuel burns as a flame visible to a user of the dispenser, wherein the steps of providing the fuel source and lighting the fuel burner include providing a visually observable use-up cue for the substantial exhaustion of volatile from the volatile carrier.

44. A kit for use with a heated volatile dispenser that employs a fuel burner to provide hot gases to heat and release a volatile material from a volatile carrier, the kit comprising:

a. at least one volatile carrier, each volatile carrier bearing a selected amount of the volatile to be dispensed; and b. at least one fuel source for the fuel burner, the amount of fuel in a selected number of fuel sources being selected to be exhausted at substantially the same time that a selected amount of the volatile has been exhausted from at least one of the volatile carriers of the kit, whereby the exhausting of fuel provides a use-up cue indicating that the selected amount of volatile has also been exhausted.

45. The kit of claim 44, wherein there is only one fuel source.

46. The kit of claim 44, wherein there is only one volatile carrier.

47. The kit of claim 44, wherein the volatile of a single volatile carrier is exhausted by the hot gases generated by the use of a single fuel source.

48. The kit of claim 44, wherein the fuel source is a candle.

49. The kit of claim 44, wherein a. each volatile carrier has a treated section that is linearly extended and holds volatile material to be dispensed; and b. the amount of volatile material held by a volatile carrier is selected to be exhausted by the hot gases generated by the use of a single fuel source when the volatile carrier is so positioned that the hot gases sweep over the linearly extended section.

50. The kit of claim 49, wherein the treated section has at least two sides and the amount of volatile material held by a volatile carrier is selected to be exhausted by the hot gases generated by the use of a single fuel source when the volatile carrier is so positioned that the hot gases sweep over the at least two sides of the linearly extended section.

51. The kit of claim 44, wherein a. each volatile carrier has a treated section that is linearly extended and holds volatile material to be dispensed, the treated section having at least two sides;

b. the volatile carrier has a leading edge; and c. the amount of volatile material held by the treated section is selected to be exhausted by exposure to a flow of hot gases generated by the use of a single fuel source when the volatile carrier is so positioned that the flow of hot gases divides, with hot gases flowing to either side of the leading edge, to sweep over the sides of the treated section.

52. A fuel burner useable with a heated volatile dispenser that has an attachment post for holding the fuel burner, the fuel burner comprising a candle held within a open-topped candle cup, the candle cup having a. cup floor;

b. cup walls;

c. a downwardly opening socket extending downwardly beneath the cup floor and engageable on the attachment post; and d. at least one cup support member extending downwardly beneath the cup floor at least as far as the socket extends, the at least one cup support member being at a location sufficiently remote from the socket and cumulatively extending circumferentially sufficiently to provide a stable support such that the candle cup can sit on a flat surface without tipping.

* * * * *